US010363255B2

(12) United States Patent
Horvath et al.

(10) Patent No.: US 10,363,255 B2
(45) Date of Patent: *Jul. 30, 2019

(54) STABLE AND SOLUBLE FORMULATIONS OF RECEPTOR TYROSINE KINASE INHIBITORS, AND METHODS OF PREPARATION THEREOF

(71) Applicant: ForSight Vision4, Inc., Menlo Park, CA (US)

(72) Inventors: Judit Horvath, Menlo Park, CA (US); Irina Astafieva, Menlo Park, CA (US); Signe Erickson, Menlo Park, CA (US); Kathleen Cogan Farinas, Menlo Park, CA (US)

(73) Assignee: FORSIGHT VISION4, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/880,180

(22) Filed: Jan. 25, 2018

(65) Prior Publication Data

US 2018/0147204 A1    May 31, 2018

Related U.S. Application Data

(63) Continuation of application No. 15/270,493, filed on Sep. 20, 2016, now Pat. No. 9,895,369, which is a continuation of application No. 14/819,682, filed on Aug. 6, 2015, now Pat. No. 9,474,756.

(60) Provisional application No. 62/035,274, filed on Aug. 8, 2014.

(51) Int. Cl.
| | |
|---|---|
| *A61K 31/506* | (2006.01) |
| *A61K 9/00* | (2006.01) |
| *A61K 9/08* | (2006.01) |
| *A61K 47/32* | (2006.01) |
| *A61K 47/20* | (2006.01) |
| *A61K 47/40* | (2006.01) |
| *A61K 9/19* | (2006.01) |
| *A61K 47/69* | (2017.01) |
| *A61K 47/10* | (2017.01) |
| *A61K 47/18* | (2017.01) |
| *A61M 5/14* | (2006.01) |

(52) U.S. Cl.
CPC .......... *A61K 31/506* (2013.01); *A61K 9/0048* (2013.01); *A61K 9/0051* (2013.01); *A61K 9/08* (2013.01); *A61K 9/19* (2013.01); *A61K 47/10* (2013.01); *A61K 47/183* (2013.01); *A61K 47/20* (2013.01); *A61K 47/32* (2013.01); *A61K 47/40* (2013.01); *A61K 47/6951* (2017.08); *A61M 5/14* (2013.01)

(58) Field of Classification Search
CPC .................................................... A61K 31/506
USPC ....................................................... 514/275
See application file for complete search history.

(56) References Cited

U.S. PATENT DOCUMENTS

| | | | |
|---|---|---|---|
| 2,564,977 A | 8/1951 | Hu et al. | |
| 2,585,815 A | 2/1952 | McLintock | |
| 2,886,497 A | 5/1959 | Butler | |
| 3,232,117 A | 2/1966 | Gilmont | |
| 3,416,530 A | 12/1968 | Ness | |
| 3,618,604 A | 11/1971 | Ness | |
| 3,641,237 A | 2/1972 | Gould et al. | |
| 3,828,777 A | 8/1974 | Ness | |
| 3,831,583 A | 8/1974 | Edmunds, Jr. et al. | |
| 3,845,201 A | 10/1974 | Haddad et al. | |
| 3,902,495 A | 9/1975 | Weiss et al. | |
| 3,914,402 A | 10/1975 | Shell | |
| 3,916,899 A | 11/1975 | Theeuwes et al. | |
| 3,926,188 A | 12/1975 | Baker et al. | |
| 3,949,748 A | 4/1976 | Malmin | |
| 3,949,750 A | 4/1976 | Freeman | |
| 3,961,628 A | 6/1976 | Arnold | |
| 3,977,404 A | 8/1976 | Theeuwes | |
| 3,995,635 A | 12/1976 | Higuchi et al. | |
| 4,008,719 A | 2/1977 | Theeuwes et al. | |
| 4,014,333 A | 3/1977 | McIntyre | |
| 4,014,334 A | 3/1977 | Theeuwes et al. | |
| 4,014,335 A | 3/1977 | Arnold | |
| 4,034,756 A | 7/1977 | Higuchi et al. | |
| 4,034,758 A | 7/1977 | Theeuwes | |
| 4,077,407 A | 3/1978 | Theeuwes et al. | |
| 4,111,201 A | 9/1978 | Theeuwes | |
| 4,111,203 A | 9/1978 | Theeuwes | |
| 4,135,514 A | 1/1979 | Zaffaroni et al. | |
| 4,160,452 A | 7/1979 | Theeuwes | |

(Continued)

FOREIGN PATENT DOCUMENTS

| | | |
|---|---|---|
| CN | 101327356 A | 12/2008 |
| CN | 101600476 A | 12/2009 |

(Continued)

OTHER PUBLICATIONS

Haaf et al., Polymer J., vol. 17, 145-152, 1985.*
Drugbank, https://www.drugbank.ca/drugs/DB06589, visited Jun. 6, 2018.*
".beta.-Cyclodextrin, Sulfobutyl Ethers, Sodium Salts." ChemicalBook. Web. Jan. 24, 2016. 1 page. <http://www.chemicalbook.com/ChemicalProductProperty_EN_CB41208906.htm>.

(Continued)

*Primary Examiner* — Taofiq A Solola
(74) *Attorney, Agent, or Firm* — Edward D. Grieff; Mintz, Levin, Cohn, Ferris, Glovsky and Popeo, P.C.

(57) ABSTRACT

The present disclosure relates to stable formulations of receptor tyrosine kinase inhibitors (TKI), e.g., pazopanib; methods of preparation thereof; and use of the disclosed formulations in sustained delivery of the active agent to a target site. The disclosure further relates to methods of converting one polymorphic Form of a TKI to another polymorphic Form and/or an amorphous form.

20 Claims, 5 Drawing Sheets

(56) References Cited

U.S. PATENT DOCUMENTS

| | | |
|---|---|---|
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,519,030 A | 5/1996 | Shigemitsu et al. |
| 5,554,132 A | 9/1996 | Straits et al. |
| 5,562,915 A | 10/1996 | Lowe et al. |
| 5,578,042 A | 11/1996 | Cumming |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,534,524 B1 | 3/2003 | Kania et al. |
| 6,551,291 B1 | 4/2003 | de Juan, Jr. et al. |
| 6,573,293 B2 | 6/2003 | Tang et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,878,714 B2 | 4/2005 | Askew et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 6,995,162 B2 | 2/2006 | Chen et al. |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,105,530 B2 | 9/2006 | Boloor et al. |
| 7,117,870 B2 | 10/2006 | Prescott |
| 7,125,905 B2 | 10/2006 | Tang et al. |
| 7,141,023 B2 | 11/2006 | Diermann et al. |
| 7,141,152 B2 | 11/2006 | Le Febre |
| 7,141,581 B2 | 11/2006 | Bender et al. |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,211,600 B2 | 5/2007 | Lipson et al. |
| 7,235,576 B1 | 6/2007 | Riedl et al. |
| 7,262,203 B2 | 8/2007 | Boloor et al. |
| 7,276,050 B2 | 10/2007 | Franklin |
| 7,297,709 B2 | 11/2007 | Dai et al. |
| 7,351,834 B1 | 4/2008 | Riedl et al. |
| 7,452,913 B2 | 11/2008 | Sun et al. |
| 7,468,065 B2 | 12/2008 | Weber et al. |
| 7,476,510 B2 | 1/2009 | Kapur et al. |
| 7,528,255 B2 | 5/2009 | Riedl et al. |
| 7,572,924 B2 | 8/2009 | Tang et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,687,643 B2 | 3/2010 | Tasker et al. |
| 7,709,049 B2 | 5/2010 | Chappa |
| 7,772,404 B2 | 8/2010 | Borchardt et al. |
| 7,883,717 B2 | 2/2011 | Varner et al. |
| 7,893,040 B2 | 2/2011 | Loftsson et al. |
| 7,897,623 B2 | 3/2011 | Riedl et al. |
| 7,906,136 B2 | 3/2011 | Wong et al. |
| 7,909,800 B2 | 3/2011 | Cazzini |
| 7,914,442 B1 | 3/2011 | Gazdzinski |

(56) References Cited

U.S. PATENT DOCUMENTS

| | | |
|---|---|---|
| 7,939,094 B2 | 5/2011 | Schwarz et al. |
| 7,943,782 B2 | 5/2011 | Henry |
| 7,960,564 B2 | 6/2011 | Borchardt et al. |
| 7,973,068 B2 | 7/2011 | Demopulos et al. |
| 7,989,631 B2 | 8/2011 | Alva et al. |
| 8,058,445 B2 | 11/2011 | Tasker |
| 8,063,091 B2 | 11/2011 | Dai et al. |
| 8,114,885 B2 | 2/2012 | Boloor et al. |
| 8,128,954 B2 | 3/2012 | Davis et al. |
| 8,277,830 B2 | 10/2012 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0250737 A1 | 11/2005 | Hughes et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0149480 A1 | 6/2007 | Ghosh et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0038317 A1 | 2/2008 | Chang et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0036827 A1 | 2/2009 | Cazzini |
| 2009/0043253 A1 | 2/2009 | Podaima |

(56) References Cited

U.S. PATENT DOCUMENTS

| | | |
|---|---|---|
| 2009/0047335 A1 | 2/2009 | Rastelli et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0312724 A1 | 12/2009 | Pipkin et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0227904 A1 | 9/2010 | Kabra et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2010/0331548 A1 | 12/2010 | Liu et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2011/0281901 A1 | 11/2011 | Gupta |
| 2012/0028918 A1 | 2/2012 | Gupta |
| 2012/0029445 A1 | 2/2012 | de Juan, Jr. et al. |
| 2012/0029470 A1 | 2/2012 | Juan, Jr. et al. |
| 2012/0040986 A1 | 2/2012 | Riedl et al. |
| 2012/0157521 A1 | 6/2012 | Kremmidiotis |
| 2013/0012531 A1 | 1/2013 | King et al. |
| 2013/0218081 A1 | 8/2013 | Roth |
| 2013/0245544 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0324942 A1 | 12/2013 | de Juan, Jr. et al. |
| 2014/0031769 A1 | 1/2014 | de Juan, Jr. et al. |
| 2014/0221941 A1 | 8/2014 | Erickson et al. |
| 2014/0358125 A1 | 12/2014 | de Juan, Jr. et al. |
| 2015/0190279 A1 | 7/2015 | Acharya et al. |
| 2015/0297402 A1 | 10/2015 | de Juan, Jr. et al. |
| 2016/0128867 A1 | 5/2016 | Bachelder et al. |
| 2016/0258855 A1 | 9/2016 | Farinas et al. |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0258634 A1 | 9/2017 | de Juan, Jr. et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |

FOREIGN PATENT DOCUMENTS

| | | |
|---|---|---|
| CN | 102365109 A | 2/2012 |
| EP | 0033042 B1 | 8/1984 |
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| JP | 01-149716 A | 6/1989 |
| JP | 01-197429 A | 8/1989 |
| JP | 2004-524866 A | 8/2004 |
| JP | 2008-523096 A | 7/2008 |
| JP | 2009-514888 A | 4/2009 |
| JP | 2009-523821 A | 6/2009 |
| JP | 2009-529968 A | 8/2009 |
| JP | 2010-521470 A | 6/2010 |
| JP | 2010-539082 A | 12/2010 |
| JP | 2011-513201 A | 4/2011 |
| JP | 2011-529916 A | 12/2011 |

(56) References Cited

FOREIGN PATENT DOCUMENTS

| | | |
|---|---|---|
| JP | 2012-525415 A | 10/2012 |
| JP | 2013-538860 A | 10/2013 |
| WO | WO-88/04573 | 6/1988 |
| WO | WO-90/07545 | 7/1990 |
| WO | WO-95/28984 A1 | 11/1995 |
| WO | WO-97/29850 | 8/1997 |
| WO | WO-98/25982 | 6/1998 |
| WO | WO-00/48660 | 8/2000 |
| WO | WO-01/26714 | 4/2001 |
| WO | WO-01/50943 | 7/2001 |
| WO | WO-01/68016 | 9/2001 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006/138609 | 12/2006 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/064752 A2 | 6/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 A2 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2009/0143288 A1 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010/088548 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/069053 A1 | 6/2011 |
| WO | WO-2011/0075481 A1 | 6/2011 |
| WO | WO-2011/079232 | 6/2011 |
| WO | WO-2011/140343 A1 | 11/2011 |
| WO | WO 2011/140343 A1 * | 11/2011 |
| WO | WO-2012/019047 A2 | 2/2012 |
| WO | WO-2012/019136 | 2/2012 |
| WO | WO-2012/019176 A2 | 2/2012 |
| WO | WO-2012/042421 A1 | 4/2012 |
| WO | WO-2012/065006 A2 | 5/2012 |
| WO | WO-2012/103060 A1 | 8/2012 |
| WO | WO-2013/003620 | 1/2013 |
| WO | WO-2013/022801 | 2/2013 |
| WO | WO-2013/033176 A1 | 3/2013 |
| WO | WO-2013/151568 A1 | 10/2013 |
| WO | WO 2014/064652 A1 * | 1/2014 |
| WO | WO-2014/064652 A2 | 5/2014 |
| WO | WO-2014/152959 A1 | 9/2014 |

OTHER PUBLICATIONS

"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.

"MAbPac SCX-10 Column For Monoclonal Antibody Variant Analysis." Dionex. Aug. 2010. 4 pages. [http://www.dionex.com/en-us/webdocs/87008-DS-MAbPac-SCX-10-Column-20Aug2010-LPN2567-03.pdf]. Web. Retrieved May 2012.

AMD Preclinical Studies. Anti-Factor D Fab Specifically Inhibits the Alternative Pathway. The Association for Research in Vision and Ophthalmology, Inc. 2010. p. 1.

Andrews, "Effect of nonsteroidal anti-inflammatory drugs on LFA-1 and ICAM-1 expression in gastric mucosa," Am J Physiol. Apr. 1994;266(4 Pt 1):G657-664.

Arakawa, Tsutomu, et. al. "Factors affecting short-term and long-term stabilities of proteins." Advanced Drug Delivery Reviews, vol. 10, No. 1, 1993, pp. 1-28.

ARVO, Agenda for the Summer Eye Research Conference, (Jul. 2009). 7 pages.

Avery et al., "Intravitreal bevacizumab (Avastin) in the treatment of proliferative diabetic retinopathy," Ophthalmology. Oct. 2006, 113(10):1695-1705.e6.

(56) References Cited

OTHER PUBLICATIONS

Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Black et al., Handbook of Biomaterial Properties, pp. 115 & 126, Chapman & Hall, 1998.
Block et al., "Solubility and dissolution of triamcinolone acetonide," Journal of Pharmaceutical Sciences, Apr. 1973; 62(4):617-621.
Breslin, C.W., et al., "Chapter 7. Slow Release Artificial Tears", *Symposium on Ocular Therapy* pp. 77-83, 1977.
Brewster and Loftsson, Advanced Drug Delivery Reviews, 59: 645-666 (2007).
Captisol® Cyclodextrins General. Captisol® FAQ Cyclodextrins General. Web. Jan. 24, 2016. <http://www.captisol.com/faq/cyclodextrins-general/>. 2 pages.
Castro et al., "Effect of COX inhibitors on VEGF-induced retinal vascular leakage and experimental corneal and choroidal neovascularization," Exp Eye Res. Aug. 2004;79(2):275-285.
Chirila et al., "The Vitreous Humor" in *Handbook of Biomaterial Properties*, eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.
Deissler et al., "VEGF-induced effects on proliferation, migration and tight junctions are restored by ranibizumab (Lucentis) in microvascular retinal endothelial cells,"Br J Ophthalmol 2008;92:839-843.
Del Amo, et al., Current & future ophthalmic drug delivery systems . . . , *Drug Discovery Today*, vol. 13, Nos. 3/4, Feb. 2008. pp. 135-143.
Donoso et al., "The role of inflammation in the pathogenesis of age-related macular degeneration," Surv Ophthalmol. Mar.-Apr. 2006;51(2):137-52.
Duvvuri et al., Drug Delivery to the Retina: Challenges and Opportunities, *Expert Opinion on Biological Therapy*, 2003, vol. 3(1): 45-56.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudana et al., Recent Perspectives in Ocular Drug Delivery, *Pharmaceutical Research*, 2008. 20 pages.
Gaudana R. et al., *Ocular Therapeutic agent Delivery*, AAPS J., 12(3): 348-360 (2010).
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Haller, An Overview of Sustained-release Drug Implants, Retinal Physician, Jan. 2008. 4 pages.
Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038;discussion 2039.
International Search Report and Written Opinion issued in International Application No. PCT/US2014/028396, dated Aug. 19, 2014. 9 pages.

Iwase et al., Topical pazopanib blocks VEGF-induced vascular leakage and neovascularization in the mouse retina but is ineffective in the rabbit, Invest. Ophthalmol. Vis. Sci. (2013) 54(1):503-11.
Janoria et al., Novel Approaches to Retinal Drug Delivery, *Expert Opinion Drug Delivery*, 2007. 4(4):371-388.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Li, et al., An electrochemical introculardrug delivery device, *Science Direct, Sensors and Actuators*. A 143 (2008) 41-48. www.sciencedirect.com, Avail online Jul. 4, 2007.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency. Oct. 21, 2010. 32 pages. Retrieved from the Internet: <http://www.ema.europa.eu/docs/en_GB/document_library/EPAR_-_Assessment_Report_-_Variation/human/000715/WC500101009.pdf>.
Melton, et al. 2017 Clinical Guide to Ophthalmic Drugs, 21st Ed., special issue of Review of Optometry, vol. 154, No. 5, (May 15, 2017) pp. 1-51.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., *Thermophysical Properties of Trehalose and Its Concentrated Aqueous Solutions*,Pharmaceutical Research, vol. 14, No. 5, 1997, pp. 578-590.
Molokhia et al, " Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", *Investigative Ophthalmology & Visual Science* 32-6 (1991) pp. 1785-1790.
MOTT Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Nutan, MTH, et al., *General Principles of Suspensions, in Pharmaceutical Suspensions From Formulation Development to Manufacturing*, editors AK Kulshreshtha, et al., Springer, 2010. pp. 39-62.
Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.
Rosenfeld, "The Latest Research: Intravitreal Bevacizumab for Proliferative Diabetic Retinopathy," Review of Ophthalmology's Retina Online, Feb. 2006 2 pages. Retrieved from the Internet: http://www.revophth.com/archive/newsletter/0206_retina.htm.
Saline (medicine)—Wikipedia, the free encyclopedia. http://web.archive.org/web/20110205192937/http://en.wikipedia.org/wiki/Saline_(medicine). Apr. 27, 2012. 4 pages.

(56) References Cited

OTHER PUBLICATIONS

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.
Soheilian et al., "Pilot Study of Intravitreal Injection of Diclofenac for Treatment of Macular Edema of Various Etiologies," Retina, Mar. 2010; 30(3): 509-515.
Stay et al. Computer Simulation of Convective and Diffusive Transport of Controlled-Release Drugs in the vitreous Humor, *Pharm Res* 2003,20(1), pp. 96-102.
Stella et al., Advanced Drug Delivery Reviews, 36: 3-16 (1999).
Theodossiadis et al., "Intravitreal administration of the anti-tumor necrosis factor agent infliximab for neovascular age-related macular degeneration," Am J Ophthalmol. May 2009;147(5):825-830.
Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.
Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.
Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.
Yao et al. (Prevention of Laser Photocoagulation Induced Choroidal Neovascularization Lesions by Intravitreal Doses of Ranibizumab in Cynomolgus Monkeys, ARVO 2009. 2 pages. abstract D906.

\* cited by examiner

STABLE AND SOLUBLE FORMULATIONS OF RECEPTOR TYROSINE KINASE INHIBITORS, AND METHODS OF PREPARATION THEREOF

RELATED APPLICATIONS

This application is a continuation of U.S. application Ser. No. 15/270,493 filed Sep. 20, 2016, issued as U.S. Pat. No. 9,895,369, which is a continuation of U.S. application Ser. No. 14/819,682 filed Aug. 6, 2015, issued as U.S. Pat. No. 9,474,756, which claims priority to U.S. Application No. 62/035,274 filed Aug. 8, 2014, the contents of each of which are incorporated herein by reference in their entireties.

FIELD OF DISCLOSURE

The present disclosure relates to stable formulations of receptor tyrosine kinase inhibitors (TKI), e.g., pazopanib; methods of preparation thereof; and use of the disclosed formulations in sustained delivery of the active agent to a target site. The disclosure further relates to methods of converting one polymorphic Form of a TKI to another polymorphic Form and/or an amorphous form.

BACKGROUND

Preparing formulations of therapeutic agents that have low solubility in water and delivering the agents to a target tissue has been a major challenge for pharmacologists and therapeutic agent delivery scientists. See Gaudana R. et al., *Ocular Therapeutic agent Delivery*, AAPS J., 12(3): 348-360 (2010). The combined effect of the unique anatomy and physiology of the eye and the low water solubility of the therapeutic agents for treating ocular diseases or disorders have frustrated the delivery of these agents to a desired target site of the eye. See Gaudana. There is, therefore, a need for formulations and delivery systems, which will allow high solubility of the therapeutic agents and improve stability and efficacy at the target tissues.

Protein kinases have been implicated in ocular diseases, not limited to, but including age related macular degeneration (hereinafter "AMD"), diabetic macular edema and proliferative diabetic retinopathy. Transmembrane receptor protein kinases exhibit an extracellular domain, capable of ligand binding. These ligand binding mechanisms trigger activation of the kinase catalytic domain which initiates a cascade of signals that controls intracellular functions.

Examples of receptor protein kinase are growth factors such as EGF, FGF, VEGF, PDGF and IGF. Elevated levels of soluble growth factors, such as vascular endothelial growth factor-A (VEGF), have been found in ocular tissues and fluids removed from patients with pathologic ocular angiogenesis. Various ocular tissues including the neurosensory retina and retinal pigmented epithelium (RPE) are known to respond to hypoxia, inflammation, and trauma by increasing VEGF expression that can lead to blood-retina barrier breakdown (i.e., enhanced vascular permeability and extracellular edema) and/or pathologic neovascularization (NV).

Delivery of therapeutic agents in the eye is challenging. Major drawbacks exist in the current delivery means because of the recurrent intravitreal injections required for chronic maintenance therapy. Repeated intravitreal injections present both a risk and a burden to patients. Endophthalmitis, retinal detachments, traumatic cataract, and increased intraocular pressure (IOP) are all potential vision-threatening sequela to the intravitreal route of administration. Moreover, monthly treatment or even monthly monitoring is a substantial burden to patients, their caregivers, and to the medical community, especially when considering that treatment may need to persist for a patient's lifetime. While roughly one-third of patients experience improved vision when treated with repeated intravitreal injections of certain biologic VEGF inhibitors, the majority of patients experience only stabilization of reduced vision.

Formulations may provide less than ideal stability in one or more ways when injected into a therapeutic device in at least some instances. For example, a buffer of the injected formulation may be released from the device into the vitreous in at least some instances. Also, diffusion of hydrogen ions and hydroxide ions between the reservoir and the vitreous may affect the pH of the formulation within the device.

In at least some instances, a buffer of a fluid of the eye such as the vitreous humor having a physiological pH may enter the device and affect the pH of the formulation within the device, such that the stability of the therapeutic agent may be less than ideal in at least some instances.

In at least some instances, formulation components added to increase the solubility of the therapeutic agents may bind the therapeutic agent so strongly that efficacy at the target tissue may be less than ideal in at least some instances.

In light of the above, it is desirable to provide improved formulations of therapeutic agents for therapeutic devices that overcome at least some of the above deficiencies of the known formulations, for example, with improved therapeutic agent release that can be maintained over an extended time when implanted.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

SUMMARY OF THE DISCLOSURE

The present disclosure relates generally to formulations of a therapeutic agent having low solubility in water. Receptor tyrosine kinase inhibitor, e.g., pazopanib, formulations and methods of preparation and use in treating and ameliorating ophthalmic diseases and/or disorders are disclosed herein.

The present disclosure provides stable pharmaceutical formulation(s) of a pharmaceutically acceptable salt of a therapeutic agent having low aqueous solubility, and one or more formulation agents, wherein the pharmaceutically acceptable salt is a monovalent or a divalent salt, and the one or more formulation agents comprise a complexing agent, a solubilizing agent, and optionally a buffering agent; wherein the salt of the therapeutic agent is in solution in the formulation. The therapeutic agent is pazopanib.

The present disclosure provides stable pharmaceutical formulation(s) of a pharmaceutically acceptable salt of a therapeutic agent having low aqueous solubility, and one or more formulation agents, wherein the pharmaceutically acceptable salt is a monovalent or a divalent salt, and the one or more formulation agents comprise a complexing agent, a solubilizing agent, and a buffering agent; wherein the salt of the therapeutic agent is in solution in the formulation. The therapeutic agent is pazopanib.

The present disclosure provides stable pharmaceutical formulation(s) of a pharmaceutically acceptable salt of a therapeutic agent having low aqueous solubility, and one or more formulation agents, wherein the pharmaceutically acceptable salt is a monovalent or a divalent salt, and the one or more formulation agents comprise a complexing agent, a solubilizing agent, but without a buffering agent; wherein the salt of the therapeutic agent is in solution in the formulation. The therapeutic agent is pazopanib.

The pharmaceutically acceptable salt is a monovalent or a divalent halide salt. The salt is a chloride salt. The monovalent salt is stable in formulation up to a concentration of about 60 mg/mL. The divalent salt is stable in formulation up to a concentration of about 70 mg/mL. The divalent salt crystal structure prior to formulation is Form XIV as determined by XRPD. The stability of the monovalent salt in the formulation is increased by performing lyophilization of the therapeutic agent from an organic solvent before solubilizing in a solution with the formulation agents. The organic solvent is dimethyl sulfoxide (DMSO) or trifluoro ethanol (TFE). The lyophilization from DMSO converts one crystalline phase form of the therapeutic agent to another form. The lyophilization from DMSO converts crystalline phase Form A to a material containing at least about 70% crystalline phase Form G, as determined by XRPD. The lyophilization from TFE converts crystalline phase Form A to partially or completely amorphous phase. The pH is adjusted during formulation of the therapeutic agent, or the pH is not adjusted during formulation of the therapeutic agent.

The solubilizing agent in the formulations and in the methods of preparing the formulations of the present disclosure is a polymer, e.g., poly(vinyl pyrrolidone) (PVP); the buffering agent, when present, is Histidine HCl; the complexing agent is a cyclodextrin is: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof; and the therapeutic agent is pazopanib (5-[[4-[(2,3-Dimethyl-2H-indazol-6-yl)methylamino]-2-pyrimidinyl]amino]-2-methylbenzolsulfonamide) salts, e.g., pazopanib 1 HCl or pazopanib 2 HCl.

The present disclosure provides a method of preparing a stable, solution pharmaceutical formulation of a pharmaceutically acceptable salt of a therapeutic agent having low aqueous solubility, wherein the salt is a divalent salt, the method comprising (a) dissolving the salt in a solution of one or more formulation agents, wherein the formulation agents comprise a complexing agent, a solubilizing agent, and optionally a buffering agent, and (b) adjusting the pH to an optimal value after dissolving the salt in the formulation agents. The present disclosure provides a method of preparing a stable, solution pharmaceutical formulation of a pharmaceutically acceptable salt of a therapeutic agent having low aqueous solubility, wherein the salt is a divalent salt, the method comprising (a) dissolving the salt in a solution of one or more formulation agents, wherein the formulation agents comprise a complexing agent, a solubilizing agent, and a buffering agent, and (b) adjusting the pH to an optimal value after dissolving the salt in the formulation agents. The present disclosure provides a method of preparing a stable, solution pharmaceutical formulation of a pharmaceutically acceptable salt of a therapeutic agent having low aqueous solubility, wherein the salt is a divalent salt, the method comprising (a) dissolving the salt in a solution of one or more formulation agents, wherein the formulation agents comprise a complexing agent, and a solubilizing agent, but without a buffering agent, and (b) adjusting the pH to an optimal value after dissolving the salt in the formulation agents.

The present disclosure provides a method of preparing a stable, solution pharmaceutical formulation of a pharmaceutically acceptable salt of a therapeutic agent having low aqueous solubility, wherein the salt is a monovalent salt, the method comprising (a) treating the salt with a base; (b) dissolving the base treated salt in a solution of one or more formulation agents, wherein the formulation agents comprise complexing agent, a solubilizing agent, and optionally a buffering agent, and (c) adjusting the pH with an acid to a pH equal to or below about 2, wherein the base treatment increases the total salt content in the formulation and the adjusting pH with acid increases solubility of the salt in the formulation.

The present disclosure provides a method of preparing a stable, solution pharmaceutical formulation of a pharmaceutically acceptable salt of a therapeutic agent having low aqueous solubility, in which the salt is a monovalent salt; the method includes (a) preparing a solution of the salt in an organic solvent; (b) lyophilizing the solution, thereby preparing a lyophilized salt of the therapeutic agent; (c) dissolving a solubilizing agent and a buffering agent in water, thereby preparing a solution; (d) dissolving a complexing agent in the solution; and (e) adding the lyophlilized salt to the solution, mixing to dissolve the salt in the solution at equal to or higher than about ambient temperature; wherein pH of the formulation is optionally adjusted.

The present disclosure provides a method of preparing a stable, solution pharmaceutical formulation of a pharmaceutically acceptable salt of a therapeutic agent having low aqueous solubility, in which the salt is a monovalent salt; the method includes (a) preparing a solution of the salt in an organic solvent (e.g., trifluoro ethanol, trifluoro ethanol-water mixture, or dimethyl sulfoxide); (b) lyophilizing the solution, thereby preparing a lyophilized salt of the therapeutic agent; (c) dissolving a solubilizing agent and a buffering agent in water, thereby preparing a solution; (d) dissolving an amount of a complexing agent in the solution, thereby preparing a low viscosity solution; (e) adding the lyophilized salt to the low viscosity solution, mixing, dissolving in the solution at equal to or higher (about 37° C.-about 50° C.) than about ambient temperature; adjusting pH of the low viscosity solution; and (f) adding and dissolving about 2× more the amount of the complexing agent to the low viscosity solution.

The lyophilizing from a polar aprotic solvent converts a crystalline phase Form A to a material containing at least about 70% Form G of pazopanib, as determined by XRPD. The lyophilized salt is dissolved in the solution at a temperature between about 37° C. to about 50° C. The lyophilizing from an organosulfur compound converts a crystalline phase Form A of pazopanib 1 HCl to a material containing up to or at least about 70% Form G of pazopanib 1 HCl, as determined by XRPD. The lyophilizing from dimethyl sulfoxide (DMSO) converts a crystalline phase Form A of pazopanib 1 HCl to a material containing up to or at least about 70% Form G of pazopanib 1 HCl, as determined by XRPD. The lyophilizing from dimethyl sulfoxide (DMSO) converts a crystalline phase Form A of pazopanib 1 HCl to a material containing about 100% Form G of pazopanib 1 HCl, as determined by XRPD. The lyophilizing step from an alcohol converts a crystalline phase Form A of pazopanib 1 HCl to an amorphous (or microcrystalline) material form of pazopanib 1 HCl, as determined by XPRD. The lyophilizing from an alcohol, e.g., trifluoroethanol (TFE), converts a crystalline phase Form A of pazopanib 1 HCl to an amorphous (or microcrystalline) material form of pazopanib 1 HCl, as determined by XPRD. The Form A of pazopanib 1 HCl is dissolved in an alcohol, e.g., TFE, or in TFE/water mixtures and then the solution is lyophilized. The lyophilized salt is dissolved in the solution at a temperature between about 37° C. to about 50° C.

The present disclosure provides a method of preparing a stable, solution pharmaceutical formulation of a pharmaceutically acceptable salt of a therapeutic agent having low aqueous solubility, in which the salt is a monovalent salt, e.g., pazopanib 1 HCl; the method includes (a) preparing a solution of the salt in an organic solvent (e.g., trifluoro ethanol, trifluoro ethanol-water mixture, or dimethyl sulfoxide); (b) lyophilizing the solution, thereby preparing a lyophilized salt of the therapeutic agent; (c) continuously mixing at least a solubilizing agent, a buffering agent, a complexing agent, and the lyophilized salt of a therapeutic agent, e.g., pazopanib 1 HCl, while adding water, at equal to or higher (e.g., about 37° C. to about 50° C.) than about ambient temperature. The pH of the formulation is adjusted to about 6 to about 7 with a base.

The present disclosure provides a method of preparing a stable, solution pharmaceutical formulation of a pharmaceutically acceptable salt of a therapeutic agent having low aqueous solubility, in which the salt is a monovalent salt, e.g., pazopanib 1 HCl; the method includes (a) preparing a solution of the salt in an organic solvent (e.g., trifluoro ethanol, trifluoro ethanol-water mixture, or dimethyl sulfoxide); (b) lyophilizing the solution, thereby preparing a lyophilized salt of the therapeutic agent; (c) continuously mixing at least a solubilizing agent, a buffering agent, a complexing agent, and the lyophilized salt of a therapeutic agent, e.g., pazopanib 1 HCl, while adding water, at equal to or higher (e.g., about 37° C. to about 50° C.) than about ambient temperature. The pH of the formulation prepared by this method is not adjusted.

The present disclosure provides a method of converting crystal Form A of pazopanib to a material containing at least about 70% crystal Form G of pazopanib, the method comprising dissolving Form A in DMSO and lyophilizing the resulting solution. The present disclosure provides a method of converting crystal Form A of pazopanib to a material containing about 100% crystal Form G of pazopanib, the method comprising dissolving Form A in DMSO and lyophilizing the resulting solution.

The present disclosure provides a use of the formulation(s) of the present disclosure in a method of treating, preventing progression of, or ameliorating a symptom of a disorder characterized by vascular leakage or neovascularization (NV) in the retina of the eye of a subject.

The present disclosure provides a use of the formulation(s) of the present disclosure in the manufacture of a medicament for use in a method of treating, preventing progression of, or ameliorating a symptom of a disorder characterized by vascular leakage or neovascularization (NV) in the retina of the eye of a subject.

The present disclosure provides a kit comprising a stable formulation(s) of the present disclosure contained in a reservoir chamber of a therapeutic device, wherein the reservoir chamber is coupled to a porous structure for controlled release of the therapeutic agent in the vitreous of the eye.

The present disclosure provides drug delivery formulation(s) of the present disclosure contained in a reservoir chamber coupled to a porous structure in a therapeutic agent delivery system for controlled release of the therapeutic agent in the vitreous of the eye; and wherein the controlled release of the formulation from the porous structure produces a concentration of the therapeutic agent in the vitreous that is lower than the concentration of the therapeutic agent in the reservoir chamber by at least two orders of magnitude.

The formulation(s) of the present disclosure is used in a method of ocular drug delivery. The formulation(s) of the present disclosure is an intravitreal delivery formulation. The formulation(s) of the present disclosure is not an eye drop. The formulation(s) of the present disclosure is not a topical delivery formulation. The formulation(s) of the present disclosure is not an oral delivery formulation or a parenteral delivery formulation. The formulation(s) of the present disclosure is not a periocular delivery formulation.

The present disclosure provides a method of treating and/or ameliorating an ophthalmic disease or disorder of the posterior segment of the eye, the method comprising delivering a stable pharmaceutical formulation of a pharmaceutically acceptable salt of a therapeutic agent having low aqueous solubility, and one or more formulation agents, from a intravitreal delivery device comprising a reservoir chamber coupled to a porous structure, wherein the formulation is contained in the reservoir of the device, and the controlled release of the formulation from the reservoir through the porous structure increases the half-life of the therapeutic agent in the vitreous; wherein the pharmaceutically acceptable salt is a monovalent or a divalent salt, and the one or more formulation agents comprise a complexing agent, a solubilizing agent, and a buffering agent; wherein the salt of the therapeutic agent is in solution in the formulation. The reservoir chamber is re-fillable and is re-filled with the formulation after the device is inserted into the eye.

The reservoir chamber is re-filled with the formulation after the device has been in the eye for between 30-90 days, or up to 6 months.

The ophthalmic disease or disorder for treating and/or ameliorating with formulation(s) of the present disclosure is: diabetic retinopathy, age-related macular degeneration (AMD), pathologic choroidal neovascularization (CNV), pathologic retinal neovascularization, uveitis, retinal vein occlusion, ocular trauma, surgery induced edema, surgery induced neovascularization, cystoid macular edema, ocular ischemia, retinopathy of prematurity, Coat's disease, sickle cell retinopathy, and/or neovascular glaucoma.

The present disclosure provides a method of converting a crystal form of pazopanib, e.g., pazopanib 1 HCl, to a material containing crystal Form G of pazopanib, the method comprising dissolving the crystal form in DMSO and lyophilizing the resulting solution; in which the at least about 70% Form G of pazopanib is formed. The present disclosure provides a method of converting a crystal form of pazopanib to a material containing crystal Form G of pazopanib, the method comprising dissolving the crystal form in DMSO and lyophilizing the resulting solution; in which the about 100% Form G of pazopanib is formed. The present disclosure provides a method of converting a crystal form of pazopanib to a material containing crystal Form G of pazopanib, the method comprising dissolving the crystal form in DMSO and lyophilizing the resulting solution; in which between about 70% to about 100% (e.g., about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%) Form G of pazopanib is formed.

The present disclosure provides a method of converting crystal Form A of pazopanib, e.g., pazopanib 1 HCl, to a material containing crystal Form G of pazopanib, the method comprising dissolving Form A in DMSO and lyophilizing the resulting solution; in which the at least about 70% Form G of pazopanib is formed. The present disclosure provides a method of converting crystal Form A of pazopanib to a material containing crystal Form G of pazopanib, the method comprising dissolving the crystal Form A in DMSO and lyophilizing the resulting solution; in which the about 100% Form G of pazopanib is formed. The present disclosure provides a method of converting crystal Form A of pazopanib to a material containing crystal Form G of pazopanib, the method comprising dissolving the crystal Form A in DMSO and lyophilizing the resulting solution; in which between about 70% to about 100% (e.g., about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%) Form G of pazopanib is formed.

In one aspect the present disclosure provides a stable pharmaceutical formulation of pazopanib 1 HCl for intravitreal delivery from a delivery device including a complexing agent, a solubilizing agent, and optionally a buffering agent. Before dissolving, pazopanib 1 HCl is lyophilized in DMSO, which converts at least about 70% crystalline phase form A of pazopanib 1 HCl to crystalline phase form G and increases stability. Pazopanib 1 HCl in the formulation thus formed does not precipitate when diluted and/or during or upon delivery into the vitreous for at least 50 days.

In one aspect the present disclosure provides a stable pharmaceutical formulation of pazopanib 1 HCl for intravitreal delivery from a delivery device including a complexing agent, a solubilizing agent, and optionally a buffering agent. Before dissolving, pazopanib 1 HCl is lyophilized in trifluoro ethanol (TFE), which converts crystalline phase form A of pazopanib 1 HCl to partially or completely amorphous and/or microcrystalline phase. Pazopanib 1 HCl in the formulation thus formed does not precipitate when diluted and/or during or upon delivery into the vitreous for at least 50 days.

The present disclosure provides a method of converting a crystal form of pazopanib to an amorphous form of pazopanib, the method comprising dissolving the crystal form in TFE and lyophilizing the resulting solution; in which up to or at least 96% amorphous pazopanib is formed.

BRIEF DESCRIPTION OF THE DRAWINGS

In order to understand the invention and to demonstrate how it may be carried out in practice, embodiments now described, by way of non-limiting example only, with reference to the accompanying drawing in which.

DETAILED DESCRIPTION

Figure 1:
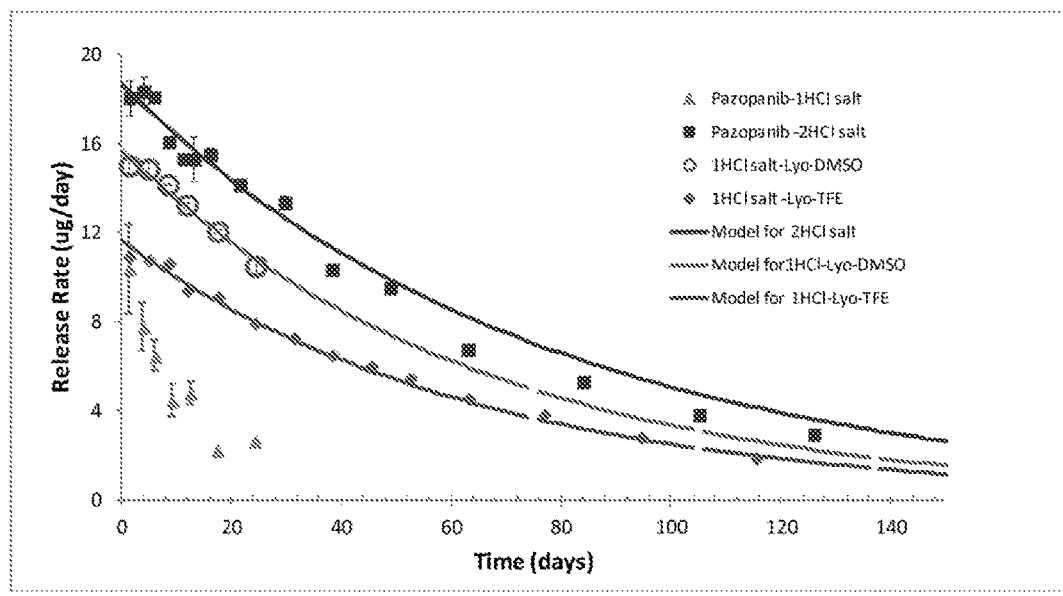
FIG. 1 shows line graphs of in vitro drug release from implants (4.5 sccm gas flow) filled with various forms of pazopanib formulated with CAPTISOL®. The measured release data is shown together with the predicted release from the diffusion model.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Also, throughout this specification, various publications are referenced. The disclosures of these publications in their entireties, unless specified to the contrary, are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Drug delivery formulations of low solubility compounds or active agents (referred to in this disclosure interchangeably) require significant investment in research and development in order to ensure that the active agent not only is stable in the formulation but is active and released at an efficacious rate over the desired treatment period. Depending on the treatment objective of a disease and/or disorder, therefore, development of formulations that meet the desired treatment objectives is desirable. Delivery of active agents for treating or ameliorating diseases and/or disorders of the posterior segment of the eye is particularly challenging because topical delivery of the active, e.g. by eye drop, rarely, if ever, results in optimal amount of active agent delivered to the target site. Moreover, the concentration required to deliver an efficacious amount of an active to a posterior eye segment target site often require high concentration of the active, which contributes to, at least, some systemic side-effects due to off-target effects. Delivery of drug formulations via injections avoids the problems with eye drops. But repeated intravitreal injections present both a risk and a burden to patients. Endophthalmitis, retinal detachments, traumatic cataract, and increased intraocular pressure (IOP) are all potential vision-threatening sequela to the intravitreal route of administration. Moreover, monthly treatment or even monthly monitoring is a substantial burden to patients, their caregivers, and to the medical community, especially when considering that treatment may need to persist for a patient's lifetime. While roughly one-third of patients experience improved vision when treated with repeated intravitreal injections of certain biologic VEGF inhibitors, the majority of patients experience only stabilization of reduced vision.

Drug delivery formulations that are developed for delivery through an intravitreal delivery device, as described in WO2010/088548, require that the active agent not only remains in solution (i.e., does not precipitate and/or agglomerate) before and during release from the device, but also that the active agent remains stable during the same period. And in order to ensure that the active is delivered to the target site at the posterior segment of the eye for an extended period of time for meeting a desired treatment goal, the active must be delivered over many days, weeks, and months. Achieving this goal is a tall order, as evident from lack of treatment options for diseases and/or disorders of the posterior eye segment despite many years of research and development, and significant financial investment by numerous entities.

The present disclosure provides formulations for delivering active agent to the posterior segment of the eye. The active agent formulations of the present disclosure are stable formulations for drug delivery over an extended period of time. The present disclosure also provides methods of preparing (and/or manufacturing) drug delivery formulations for delivering active agents that are insoluble or have low solubility in aqueous solutions. The formulations prepared (and/or manufactured) by the methods of the present disclosure are delivered from an intravitreal delivery device of the present disclosure.

Therapeutic agent delivery from a diffusion controlled device requires a source of therapeutic agent with a dissolved therapeutic agent concentration higher in energy than the therapeutic agent concentration in the target tissue. Delivery of some therapeutic agents is limited by the dissolved therapeutic agent concentration and thermodynamic energy achievable in the source formulation loaded into the device.

It is desirable to deliver therapeutic levels of therapeutic agent for periods of, for example, three months. This is particularly challenging for therapeutic agents with aqueous solubility not much greater than levels needed to be therapeutic in the tissue. For example, target concentrations in the vitreous of about 0.1-10 µg/mL is not achievable from a diffusion controlled therapeutic device implant if the therapeutic agent solubility in aqueous solution is no more than 1-10 µg/mL as is the case for many therapeutic agents, including tyrosine kinase inhibitors.

Furthermore, some formulation approaches increase the amount of therapeutic agent in a formulation that is not in solid form but the formulated entities in solution are large in size and have diffusion rates that are slower than individually dissolved therapeutic agent molecules. For example, several therapeutic agent molecules may associate or self-assemble into a structure such as a micelle, with a size that is an order of magnitude larger than a single therapeutic agent molecule and a diffusion rate that is an order of magnitude slower. Furthermore, the size of the diffusing species increases with time in a reproducible or irreproducible manner, resulting in delivery rate profiles from a diffusion controlled device that drop with time and fail to meet sustained delivery target profiles for extended amounts of time.

The present disclosure provides stable pharmaceutical formulations of a pharmaceutically acceptable salt of a therapeutic agent having low aqueous solubility, and one or more formulation agents. The pharmaceutically acceptable salt is a monovalent or a divalent salt, and the one or more formulation agents include at least a complexing agent, a solubilizing agent, and a buffering agent. The salts of the therapeutic agent are dissolved in the pharmaceutical formulations of the present disclosure. The formulations provided in the present disclosure are pazopanib formulations. The formulation is a pharmaceutically acceptable monovalent or a divalent salt, e.g., a halide salt. The present disclosure provides stable pharmaceutical formulations of pazopanib mono- and/or di-chloride salt.

The present disclosure provides that the number of salt molecules (e.g., 1 HCl or 2 HCl) and the polymorphic Form influences the solubility and/or stability of the therapeutic agent in formulation. Depending on whether 1 HCl or 2 HCl is present and/or polymorphic Forms of the salts, achieving a stable and/or soluble formulation of the pharmaceutically acceptable salt of the therapeutic agent requires different methods of preparing the formulations. Moreover, the present disclosure provides methods for altering one polymorphic form of the pharmaceutically acceptable salt of the therapeutic agent to another polymorphic form. The methods provide an altered polymorphic form with higher solubility of the pharmaceutically acceptable salt of the therapeutic agent in the formulation. The methods provide dissolving active agent in formulations as an partial and/or complete amorphous form. Accordingly, the present disclosure provides stable and/or highly soluble formulations of polymorphic Forms of a pharmaceutically acceptable salt of a therapeutic agent characterized as having low aqueous solubility or is insoluble in an aqueous solution.

Solubility of the therapeutic agents in water or an aqueous solvent may vary from being sparingly soluble (parts of solvent required for 1 part of solute being 30 to 100), slightly soluble (parts of solvent required for 1 part of solute being 100 to 1000), very slightly soluble (parts of solvent required for 1 part of solute being 1000 to 10,000), and practically insoluble or insoluble (≥10,000). Therapeutic agents of the present invention may be a poor or low water soluble compound. As referred to herein, a poor or low water soluble compound may have a solubility of, for example, less than 1 mg/mL or less than 0.01 mg/mL.

Formulation

The formulations of the current disclosure are formulated to achieve high concentration (about 1 mg/mL-about 300 mg/mL) of a therapeutic agent, which is characterized as being not soluble in water or is poorly soluble in water.

Complexing agents, such as cyclodextrins, which do not cross biological membranes easily and do not affect the PK properties of the therapeutic agents, are used to increase the aqueous concentration of the agent in the reservoir of the therapeutic device of the current disclosure. Complexing agents, e.g., cyclodextrin formulations, of the present disclosure, increase the concentration of dissolved therapeutic agent up to 800,000 fold, as high as about 10 mg/mL to about 100 mg/mL for therapeutic agents with aqueous solubility of 10 mg/mL or less, e.g., therapeutic agents with aqueous solubility of about 0.1 µg/mL or less.

The present disclosure provides formulations of a therapeutic agent, e.g., pazopanib mono- or di-hydrochloride, where the concentration in the device and/or at the target upon delivery is between about 10 mg/mL to up to about 70 mg/mL (e.g., about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL). The present disclosure provides about 30 mg/mL to about 50 mg/mL of pazopanib in the formulation.

The measured concentration is between about 10 mg/mL to up to about 70 mg/mL (e.g., about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL).

The present disclosure provides fill concentration of the therapeutic agent, e.g., pazopanib 1 HCL or 2 HCL, in the delivery device is between about 10 mg/mL to up to about 70 mg/mL (e.g., about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL).

The present disclosure provides monovalent halide salt, e.g., chloride salt, of pazopanib that is stable in the disclosed formulations, in a delivery device, at about 10 mg/ml, about 15 mg/ml, about 20 mg/ml, about 25 mg/ml, about 30 mg/ml, about 35 mg/ml, about 45 mg/ml, about 50 mg/ml, about 55 mg/ml, about 60 mg/ml, about 65 mg/ml, about 70 mg/ml, about 75 mg/ml, or about 80 mg/ml. The present disclosure provides monovalent halide salt, e.g., chloride salt, of pazopanib that is stable in the disclosed formulations, in a delivery device, at about 10 mg/ml up to about 15 mg/ml, about 15 mg/ml up to about 20 mg/ml, about 20 mg/ml up to about 25 mg/ml, about 25 mg/ml up to about 30 mg/ml, about 30 mg/ml up to about 35 mg/ml, about 35 mg/ml up to about 45 mg/ml, about 45 mg/ml up to about 50 mg/ml, about 50 mg up to about 55 mg/ml, about 55 mg/ml up to about 60 mg/ml, about 60 mg/ml up to about 65 mg/ml, about 65 mg/ml up to about 70 mg/ml, about 70 mg/ml up to about 75 mg/ml, or about 75 mg/ml up to about 80 mg/ml. The monovalent halide salt, e.g., chloride salt, of pazopanib that is stable in the disclosed formulations at about 40 mg/ml to up to about 60 mg/ml.

The present disclosure provides divalent halide salt, e.g., chloride salt, of pazopanib that is stable in the disclosed formulations, in a delivery device, at about 10 mg/ml, about 15 mg/ml, about 20 mg/ml, about 25 mg/ml, about 30 mg/ml, about 35 mg/ml, about 45 mg/ml, about 50 mg/ml, about 55 mg/ml, about 60 mg/ml, about 65 mg/ml, about 70 mg/ml, about 75 mg/ml, or about 80 mg/ml. The present disclosure provide divalent halide salt, e.g., chloride salt, of pazopanib that is stable in the disclosed formulations, in a delivery device, at about 10 mg/ml to about 15 mg/ml, about 15 mg/ml to about 20 mg/ml, about 20 mg/ml to about 25 mg/ml, about 25 mg/ml to about 30 mg/ml, about 30 mg/ml to about 35 mg/ml, about 35 mg/ml to about 45 mg/ml, about 45 mg/ml to about 50 mg/ml, about 50 mg to about 55 mg/ml, about 55 mg/ml to about 60 mg/ml, about 60 mg/ml to about 65 mg/ml, about 65 mg/ml to about 70 mg/ml, about 70 mg/ml to about 75 mg/ml, or about 75 mg/ml to about 80 mg/ml. The divalent pazopanib halide salt, e.g., chloride salt, of the present disclosure is stable in the disclosed formulations at about 60 mg/ml.

The complexing agent is sulfobutyl ether-β-cyclodextrin ("SBEβCD") or CAPTISOL®. The formulations intravitreal delivery of the current disclosure comprises therapeutic agent pazopanib mono- or di-hydrochloride in a complex with CAPTISOL®. Association of therapeutic agent pazopanib mono- or di-hydrochloride with CAPTISOL® increases aqueous solubility of the agent by a factor of 10 to 25,000. Interaction of therapeutic agent pazopanib mono- or di-hydrochloride with CAPTISOL® provides a beneficial and protected environment for the therapeutic agent in the lipophilic cavity of CAPTISOL®, while the hydrophobic surface of CAPTISOL® provides effective water solubility, thereby boosting both solubility and stability of the therapeutic agent. Furthermore, interaction of the therapeutic agents with CAPTISOL® reduces decomposition of the agent by protecting labile regions from the potential reactants in the aqueous environment.

The formulations of the current disclosure comprise pazopanib or pazopanib mono- or di-hydrochloride associated with a complexing agent, e.g., cyclodextrin ("CD"), is, without being limiting to the list herein, 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof. The CD in the formulation is present at a ratio to a therapeutic agent of about 9:1, about 8:1, about 7:1, about 6:1, about 5:1, about 4:1, about 3:1, or about 2:1. The ratio of CD:therapeutic agent is about 2.5:1. The CD:therapeutic agent ratio is about 2.2:1; about 2.5:1; about 3.7:1; about 5:1; about 8:1; or about 9:1.

The increase in the concentration of the therapeutic agent in the device is about 100× higher than the concentration required at the vitreous for effective treatment, prevention of progression, or amelioration of vascular leakage and neovascularization (NV) in the retina. Because the required concentration at the vitreous for effective treatment, prevention of progression, or amelioration of vascular leakage and neovascularization (NV) is higher than the solubility limit of the therapeutic agent, the embodiments of the current disclosure provide increased therapeutic agent solubility of about or more than 1000× the inherent aqueous solubility of the agent.

The formulations of the present disclosure comprise CAPTISOL® as the complexing agent. The concentration of the therapeutic agent in the presence of CAPTISOL® is in a drug delivery agent and/or, upon delivery, in the vitreous, between 0.5 mg/mL to about 90 mg/mL. For example, the concentration of pazopanib mono- or di-hydrochloride in the presence of CAPTISOL® is about 20 mg/mL, about 30 mg/mL, about 40 mg/mL, about 50 mg/mL, about 60 mg/mL, about 70 mg/mL, about 80 mg/mL, or about 90 mg/mL.

Additional components of the formulation are: trehalose, methylcellulose, ethylcellulose, sodium carboxymethylcellulose, hydroxypropylmethylcellulose, sodium hyaluronate, sodium alginate, chitosan and its derivatives, polyethylene glycol, glycerin, propylene glycol, Triacetin, N,N-Dimethylacetamide, pyrrolidone, dimethyl sulfoxide, ethanol, N-(-beta-Hydroxyethyl)-lactamide, 1-Methyl-2-pyrrolidinone, triglycerides, monothioglycerol, sorbitol, lecithin, methylparaben, propylparaben, polysorbates, block copolymers of ethylene oxide and propylene oxide, di-block polymers or tri-block copolymers of polyethylene oxide and polypropylene oxide, ethoxylated emulsifiers, polyethylene glycol esters, sucrose laurate, Tocopherol-PEG-succinate, phospholipids and their derivatives, or other non-ionic self-emulsifying agents.

Solubilizing agents in the formulation of the current disclosure include, without being a limiting example, trehalose, methylcellulose, ethylcellulose, sodium carboxymethylcellulose, sodium hyaluronate, sodium alginate, polyethylene glycol, glycerin, propylene glycol, Triacetin, N,N-Dimethylacetamide, poly(vinyl pyrrolidone), pyrrolidone, or any combination(s) thereof. The solubilizing agent used in the preparation of formulations of the present disclosure is poly(vinyl pyrrolidone) (PVP). For example, the formulations of the current disclosure comprise between about 0.2% to about 1% PVP. The present disclosure provides, formulations with between about 5 mg/mL PVP to about 30 mg/mL PVP.

The solubilizing agent added to the formulations of the present disclosure comprises between about 0.1% to about 5.0% (e.g., about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%) PVP. The formulations of the present disclosure comprise, e.g., about 1% PVP.

The formulations of the present disclosure include a buffering agent, e.g., Histidine HCl. The formulations include about 5 mg/mL to about 30 mg/mL buffering agent, e.g., Histidine HCl, (e.g., about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL).

The pH of the formulations is between about 1.0-about 7.0 (e.g., pH of about 1.0, about 1.1, about 1.2, about 1.3, about 1.4, about 1.5, about 1.6, about 1.7, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0).

Additional additives for including in the formulations of the present disclosure are, without being a limiting example, triacetine (about 1× molar ration to the therapeutic agent), L-Lysine (about 25 mg/mL), ammonium acetate about 0.1%-about 5% (w/v) (e.g., about 2% (w/v)), or glycerol about 0.1%-about 5% (w/v) (e.g., about 2% (w/v)).

The formulation of the current disclosure includes one or two agents for pH adjustment for increasing buffering capacity of the formulation in the therapeutic device. One or two pH adjustment agents is/are selected from, without being a limiting example, sodium hydroxide, hydrochloric acid, citric acid, malic acid, acetate, tartaric acid, histidine, phosphate, or any combination(s) thereof. In one embodiment, the formulation comprises agents for pH adjustment, but no complexing agents. The one or two pH adjusting agents are citric acid and/or histidine.

The formulation of the current disclosure includes a tonicity adjusting agent. For example, the tonicity adjusting agent is, without being a limiting example, sodium chloride, sodium phosphate, or any combination(s) thereof.

The formulations of the current disclosure have high stability during the use time of the PDS implant. For example, formulations are stable in the PDS reservoir chamber at 37° C. at physiological conditions for at least 6 months. For example, the formulations are stable in the PDS in the presence of vitreous components diffusing from the vitreous.

The formulations of the present disclosure are used in a method of ocular drug delivery. The formulations of the present disclosure are intravitreal delivery formulation. The formulations of the present disclosure are not formulated as eye drops. The formulations of the present disclosure are not formulated for topical delivery. The formulations of the present disclosure are not formulated for oral delivery or parenteral delivery. The formulations of the present disclosure are not formulated for periocular delivery.

Methods of Preparation

The present disclosure provides methods of preparing and/or manufacturing a stable and in solution pharmaceutical formulation of pharmaceutically acceptable salts of pazopanib.

The present disclosure provides drug formulation processes that depend on the sample of the active agent and, therefore, the characteristics of the active in a given sample. This disclosure provides formulation processes depending on the salt forms and the crystallinity of the active agent. Tables 1, 2, and 3 provide summaries of the characteristics of the active pazopanib of the present disclosure.

TABLE 1 pH Comparison of pazopanib/CAPTISOL ® solutions with similar composition:

| Pharmaceutical ingredient in Sample | Water, mL | CAPTISOL ® mg (1.5x molar ratio to drug) | Pazopanib salt, mg | pH, measured |
|---|---|---|---|---|
| N/A - CAPTISOL ® only | 1 | 157.35 | 0 | 6.60 |
| Pazopanib-Sample 1 | 1 | 157.79 | 22.40 | 1.68 |
| Pazopanib-Sample 2-lyophilized-TFE (1HCl)* | 1 | 157.53 | 22.65 | 3.34 |
| Pazopanib-Sample 2 (1HCl)* | 1 | 157.28 | 22.41 | 3.36 |

*Based on its XRD pattern, Sample-2 has crystal structure as Form-A, which contains one HCl per drug molecule.

Chloride content comparison: Table 2 provides chloride content of various API samples, as measured by X-ray Fluorescence (XRF). See Evans Analytical Laboratories, X-Ray Fluorescence (XRF) Analysis Report, 21 Feb. 2014, Job Number C0ELG412.

TABLE 2

| | Drug sample | | |
|---|---|---|---|
| Element | Pazopanib-Source2--lyophilized-TFE HEL-1 | Pazopanib-Sample-2 HE-14 | Pazopanib-Sample = 1 MA |
| C | 41.9 | 41.7 | 37.8 |
| N | 27.7 | 29.5 | 26.4 |
| O | 11.2 | 11.3 | 10 |
| F | 3.6 | — | 1.2 |
| Al | — | — | 0.004 |
| Si | — | — | 0.026 |

TABLE 2-continued

| | Drug sample | | |
|---|---|---|---|
| Element | Pazopanib-Source2--lyophilized-TFE HEL-1 | Pazopanib-Sample-2 HE-14 | Pazopanib-Sample = 1 MA |
| S | 7.34 | 8.29 | 7.72 |
| Cl | 8.22 | 9.2 | 16.7 |
| Ca | — | — | 0.01 |
| Fe$^b$ | 0.012 | 0.009 | 0.051 |
| Ni$^b$ | 0.01 | 0.006 | — |
| Zn | — | — | 0.008 |
| Br | — | — | 0.005 |

Sample Compositions (in wt %) - normalized to 100% of the measured and detected elements From the results of the pH and the chloride content analysis it is concluded that the pharmaceutical ingredient from sample-1 contains 2-HCl per each pazopanib molecule, compared to active from sample-2, which contains only 1 HCl/per drug molecule.

Divalent Salt

The present disclosure provides a method for preparing a formulation of a divalent salt of pazopanib. The method includes the steps of (a) dissolving a divalent salt of pazopanib in a solution of one or more formulation agents. The formulation agents used in the method include, but without being limited to, a complexing agent, a solubilizing agent, and a buffering agent. The pH of the solution after dissolving the divalent salt in the solution of formulation agents is adjusted to an optimal pH for maintaining stability of the divalent salt in the formulation before and/or after release, solubility of the divalent salt in the formulation before and/or after release, release rate of the divalent salt in the formulation from a delivery device, and/or therapeutic efficacy of pazopanib upon release into the posterior segment of the eye. The pharmaceutically acceptable salt is a divalent halide salt of pazopanib, e.g., a divalent chloride salt of pazopanib, a divalent bromide salt of pazopanib, a divalent iodide salt of pazopanib, or a divalent fluoride salt of pazopanib. The present disclosure provides a method of preparing divalent chloride salt of pazopanib.

The divalent chloride salt in the formulation of pazopanib prepared by the method of the present disclosure is polymorphic Form XIV having a XRPD diffraction peaks 7.8, 12.4, 22.9, 23.6 and 26.9±0.2 degrees at 2θ (further characterized by peaks at 14.8, 17.5, 19.0, 25.3 and 27.4±0.2 degrees at 2θ); or Form I having a XRPD diffraction peaks 6.7, 7.4, 12.0, 14.8, 23.6±0.2 degrees at 2θ (further characterized by peaks at 13.3, 14.8, 19.0, 26.6±0.2 degrees at 2θ); or Form XV having XRPD diffraction peaks 6.9, 12.1, 23.6, 26.8 and 27.4±0.2 degrees at 2θ (further characterized by peaks at 15.7, 19.4, 23.3, and 25.7±0.2 degrees at 2θ). The present disclosure provides a method of preparing a formulation of polymorphic Form XIV of pazopanib dihydrochloride having a XRPD diffraction peaks 7.8, 12.4, 22.9, 23.6 and 26.9±0.2 degrees at 2θ (further characterized by peaks at 14.8, 17.5, 19.0, 25.3 and 27.4±0.2 degrees at 2θ).

The complexing agent used in the method of preparing a divalent salt formulation of pazopanib is a Cyclodextrin, e.g., 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β- cyclodextrin, hydroxypropyl-γ-cyclodextrin, randomly methylated-γ-cyclodextrin, trimethyl-γ-cyclodextrin, or any combination(s) thereof.

The solubilizing agent used in the method for preparing a formulation of a divalent salt of pazopanib of the present disclosure is poly(vinyl pyrrolidone) (PVP). The buffering agent used in the method for preparing a formulation of a divalent salt of pazopanib of the present disclosure is Histidine HCl.

The method of the present disclosure provides formulation of 2 HCl per each pazopanib molecule to formulate up to about 60 mg/ml drug concentrations. The drug is dissolved in CAPTISOL® solution, formulation agents are then added before pH is adjusted.

Formulations are prepared by dissolving the required amount of pazaopanib 2 HCl salt in cyclodextrin, acid, and formulation agents in water. Pazaopanib 2 HCl is added and mixed until dissolution. Then sodium hydroxide is added to reach the final pH. Formulation is filtered and then injected into PDS implants to perform therapeutic agent release testing.

The present disclosure provides formulations of a therapeutic agent, e.g., pazopanib di-hydrochloride (2 HCl) and making of preparing thereof, where the active agent is stable in formulation for an extended period (i.e., more than 60 days and/or more than 90 days). Formulations with the stable active agent, e.g., pazopanib 2 HCl, have up to about 70 mg/mL active agent. The present disclosure provides formulation of pazopanib 2 HCl having up to about 10 mg/mL, up to about 11 mg/mL, up to about 12 mg/mL, up to about 13 mg/mL, up to about 14 mg/mL, up to about 15 mg/mL, up to about 16 mg/mL, up to about 17 mg/mL, up to about 18 mg/mL, up to about 19 mg/mL, up to about 20 mg/mL, up to about 21 mg/mL, up to about 22 mg/mL, up to about 23 mg/mL, up to about 24 mg/mL, up to about 25 mg/mL, up to about 26 mg/mL, up to about 27 mg/mL, up to about 28 mg/mL, up to about 29 mg/mL, up to about 30 mg/mL, up to about 31 mg/mL, up to about 32 mg/mL, up to about 33 mg/mL, up to about 34 mg/mL, up to about 35 mg/mL, up to about 36 mg/mL, up to about 37 mg/mL, up to about 38 mg/mL, up to about 39 mg/mL, up to about 40 mg/mL, up to about 41 mg/mL, up to about 42 mg/mL, up to about 43 mg/mL, up to about 44 mg/mL, up to about 45 mg/mL, up to about 46 mg/mL, up to about 47 mg/mL, up to about 48 mg/mL, up to about 49 mg/mL, up to about 50 mg/mL, up to about 51 mg/mL, up to about 52 mg/mL, up to about 53 mg/mL, up to about 54 mg/mL, up to about 55 mg/mL, up to about 56 mg/mL, up to about 57 mg/mL, up to about 58 mg/mL, up to about 59 mg/mL, up to about 60 mg/mL, up to about 61 mg/mL, up to about 62 mg/mL, up to about 63 mg/mL, up to about 64 mg/mL, up to about 65 mg/mL, up to about 66 mg/mL, up to about 67 mg/mL, up to about 68 mg/mL, up to about 69 mg/mL, or up to about 70 mg/mL of the stable active.

Monovalent Salt

The present disclosure provides a method for preparing a stable and/or soluble formulation of a monovalent salt of a therapeutic agent. The monovalent salt is highly insoluble in aqueous solutions and is prone to precipitation during storage, and/or before and/or after delivery of the formulation into a target site. The present disclosure provides methods of increasing ease of solubilizing the monovalent salt and/or increasing the stability of the monovalent in solution. The methods provide increased solubility and/or stability of the monovalent salt in formulation such that the salt remains dissolved during storage, and/or before and/or after delivery into a target site for an extended period of time.

To dissolve the drug, e.g., monohydrochloride of pazopanib, in one method of the present disclosure, long solubilization time and extra acid addition is necessary; the pH of the formulation is adjusted with hydrochloric acid (HCl) to equal or to below about pH=2. After a long solubilization process of the drug and the excipients (1-3 days) in CAPTISOL® solutions with pH below about 2, the pH is adjusted.

NaOH pretreatment of the drug (amorphization) is also successfully employed prior to the solubilization step at low pH. While the amorphization step reduces the time required to prepare high concentration solutions, however, this step also significantly increases the total salt content of the formulation.

The present disclosure provides a method of preparing a stable pharmaceutical formulation of a pharmaceutically acceptable monovalent salt of a therapeutic agent having low aqueous solubility. The method of preparing a stable pharmaceutical formulation of a monovalent salt of a therapeutic agent includes the steps of: (a) treating the monovalent salt with a base (amortization); (b) dissolving the base treated salt in a solution of one or more formulation agents; and (c) adjusting the pH with an acid to a pH equal to or below about 4, equal to or below about 3, equal to or below about 2, or equal to or below about 1. The formulation agents used in the method include, but not limited to, a complexing agent, a solubilizing agent, and a buffering agent. The base treatment of the monovalent salt increases the total salt content in the formulation. Adjusting the pH with acid increases solubility of the salt in the formulation.

The present disclosure provides a method of preparing a stable pharmaceutical formulation of a pharmaceutically acceptable monovalent salt of pazopanib. The method of preparing a stable pharmaceutical formulation of a monovalent salt of pazopanib, e.g., a monovalent chloride salt of pazopanib, a monovalent bromide salt of pazopanib, a monovalent iodide salt of pazopanib, or a monovalent fluoride salt of pazopanib, includes the steps of: (a) treating the monovalent salt with a base; (b) dissolving the base treated salt in a solution of one or more formulation agents; and (c) adjusting the pH with an acid to a pH equal to or below about 4, equal to or below about 3, equal to or below about 2, or equal to or below about 1. The formulation agents used in the method include, but not limited to, a complexing agent, a solubilizing agent, and a buffering agent. The base treatment of the monovalent salt increases the total salt content in the formulation. Adjusting the pH with acid increases solubility of the salt in the formulation. The base is, e.g., sodium hydroxide (NaOH). The acid is, e.g., hydrochloric acid (HCl).

The complexing agent used in the method of preparing a monovalent salt formulation of pazopanib is a cyclodextrin, e.g., 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof.

The solubilizing agent used in the method for preparing a formulation of a monovalent salt of pazopanib of the present disclosure is poly(vinyl pyrrolidone) (PVP). The buffering agent used in the method for preparing a formulation of a monovalent salt of pazopanib of the present disclosure is Histidine HCl.

The solubilizing agent used in the method for preparing a formulation of a monovalent salt of pazopanib of the present disclosure is poly(vinyl pyrrolidone) (PVP), and without any buffering agent.

The present disclosure provides considerably improved stability of the 1 HCl pazopanib formulations by lowering the drug concentration to below 40 mg/mL.

The active is prone to precipitation at high concentration. The present disclosure provides methods of preparing stable, solution formulation of a low solubility active, e.g., pazopanib.

The present disclosure provides formulations of a therapeutic agent, e.g., pazopanib monohydrochloride (1 HCl) and methods of preparing thereof, where the active agent is stable in formulation for an extended period (i.e., more than 60 days and/or more than 90 days) at lower than or higher than about 40 mg/mL. Formulations, with the stable active agent, e.g., pazopanib 1 HCl, are stable up to about 60 mg/mL. The present disclosure provides formulation of pazopanib 1 HCl having up to about 10 mg/mL, up to about 11 mg/mL, up to about 12 mg/mL, up to about 13 mg/mL, up to about 14 mg/mL, up to about 15 mg/mL, up to about 16 mg/mL, up to about 17 mg/mL, up to about 18 mg/mL, up to about 19 mg/mL, up to about 20 mg/mL, up to about 21 mg/mL, up to about 22 mg/mL, up to about 23 mg/mL, up to about 24 mg/mL, up to about 25 mg/mL, up to about 26 mg/mL, up to about 27 mg/mL, up to about 28 mg/mL, up to about 29 mg/mL, up to about 30 mg/mL, up to about 31 mg/mL, up to about 32 mg/mL, up to about 33 mg/mL, up to about 34 mg/mL, up to about 35 mg/mL, up to about 36 mg/mL, up to about 37 mg/mL, up to about 38 mg/mL, up to about 39 mg/mL, up to about 40 mg/mL, up to about 41 mg/mL, up to about 42 mg/mL, up to about 43 mg/mL, up to about 44 mg/mL, up to about 45 mg/mL, up to about 46 mg/mL, up to about 47 mg/mL, up to about 48 mg/mL, up to about 49 mg/mL, up to about 50 mg/mL, up to about 51 mg/mL, up to about 52 mg/mL, up to about 53 mg/mL, up to about 54 mg/mL, up to about 55 mg/mL, up to about 56 mg/mL, up to about 57 mg/mL, up to about 58 mg/mL, up to about 59 mg/mL, or up to about 60 mg/mL of the stable active.

The present disclosure provides methods for improving stability of 1 HCl pazopanib formulation by performing lyophilization the active agent before solubilization. The present disclosure provides formulation processes (methods of preparing formulations) for improving solubility and stability of 1 HCl pazopanib in formulations by performing lyophilization the active agent before solubilization in the formulation agents.

The present disclosure provides testing the effects of lyophilization from two different solvents (trifluoro ethanol (TFE) and dimethyl sulfoxide (DMSO)) on the crystal structure and/or the amorphous content of active agent from sample-2.

The pazopanib salts of the present disclosure are in crystalline and/or amorphous forms. A summary of XRPD results for various pazopanib salts used in formulations of the present disclosure is provided in Table 3.

TABLE 3

| API | Phases Identified by XRPD | % Crystallinity |
| --- | --- | --- |
| Pazopanib monovalent salt (1HCl) | Form A | about 100.0 |
| Pazopanib divalent salt (2HCl) | Form XIV | about 100.0 |
| Pazopanib monovalent salt (1HCl), Lyophilized from DMSO; | Form G | about 70.7 |
| Pazopanib monovalent salt (1HCl), Lyophilized from TFE; | Amorphous | about 3.9 |

Lyophilization is performed, by standard methods in the art, from trifluoro ethanol (TFE), trifluoro ethanol-water (90-10) mixture or from dimethyl sulfoxide (DMSO).

The lyophilization conditions from DMSO of the present disclosure include conditions described in Table 4 below:

TABLE 4

| Step # | Operation | Temperature (° C.) | Duration (min) |
| --- | --- | --- | --- |
| Thermal Treatment | | | |
| 3 | Hold | about 2-about 7 | 20-40 |
| 4 | Ramp | about −30 to about −50 | 100-130 |
| 5 | Hold | about −30 to about −50 | 40-80 |
| Primary Drying | | | |
| Chill Condenser and Set Vacuum Control for the following steps | | | |
| 6 | Ramp | about −5.0 to about +5.0 | 80-150 |
| 7 | Hold | about −5.0 to about +5.0 | 700-1100 |
| 8 | Ramp | about 30 to about 50 | 300-400 |
| 9 | Hold | about 30 to about 50 | 400-800 |
| Secondary Drying | | | |
| Set Vacuum Control for the Following Steps | | | |
| 10 | Ramp | about 30 to about 70 | 80-120 |
| 11 | Hold | about 30 to about 70 | 1200-1900 |

The present disclosure provides methods of preparing a stable pharmaceutical formulation of a pharmaceutically acceptable monovalent salt of a therapeutic agent having low aqueous solubility.

The present disclosure provides a crystalline form of a therapeutic agent pretreated prior to formulation process. The present disclosure provides lyophilizing a therapeutic agent, e.g., pazopanib 1 HCl, from an alcohol, thereby converting a crystalline phase Form A of pazopanib 1 HCl to an amorphous (or microcrystalline) material form of pazopanib 1 HCl, as determined by XPRD. The lyophilizing from an alcohol, e.g., trifluoroethanol (TFE), converts a crystalline phase Form A of pazopanib 1 HCl to an amorphous (or microcrystalline) material form of pazopanib 1 HCl, as determined by XPRD. The Form A of pazopanib 1 HCl is dissolved in an alcohol, e.g., TFE, or in TFE/water mixtures and then the solution is lyophilized. The lyophilized salt is dissolved in the solution at a temperature between about 37° C. to about 50° C. The present disclosure provides a method of converting a crystal form of pazopanib to an amorphous (or microcrystalline) form of pazopanib, the method comprising dissolving the crystal form in trifluoro ethanol (TFE) and lyophilizing the resulting solution; wherein up to or at least 96% amorphous pazopanib is formed.

The crystalline form of the therapeutic agent, e.g., pazopanib monohydrochloride, is pretreated by lyophilization. For example, about 60 mg/mL of a therapeutic agent, e.g., pazopanib monohydrochloride, solution in TFE is prepared. About 1% to about 30% water (e.g., about 20%) water is also added to the solution of the therapeutic agent, e.g., pazopanib monohydrochloride, solution in TFE. The solution is then freeze dried (with or without the added water) under standard condition in the art. The solution is dried under about 35° C.-about 50° C. (e.g., about 40° C.) for about 12 hours to about 24 hours or at about 50° C.-about 65° C. (e.g., at about 60° C.) for about 4-about 8 hours. The lyophilization from TFE converts crystalline phase Form A to partially or completely (e.g., up to or at least 96%) amorphous phase. The amorphous (or microcrystalline) pazopanib monohydrochloride, i.e., the lyophilized in TFE, is then dissolved in the solution prepared by mixing at least a solubilizing agent, a buffering agent, and a complexing agent, as described in the present disclosure.

The methods of converting a crystal form (e.g., Form A) of pazopanib to a material containing amorphous form provide up to about 80%, up to about 81%, up to about 82%, up to about 83%, up to about 84%, up to about 85%, up to about 86%, up to about 87%, up to about 88%, up to about 89%, up to about 90%, up to about 91%, up to about 92%, up to about 93%, up to about 94%, up to about 95%, or up to about 96% amorphous pazopanib 1 HCl. Alternatively, the methods provide that at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% amorphous pazopanib 1 HCl is formed. The remaining active agent is in crystalline form, either in the original Form, or in a mixture of the original or another Form (e.g., Form A and/or Form G).

The present disclosure provides lyophilizing a therapeutic agent, e.g., pazopanib 1 HCl, from a polar aprotic solvent for converting one crystalline phase Form, e.g., crystalline phase Form A of pazopanib 1 HCl, to a material containing up to or at least about 70% different crystalline phase form, e.g., Form G of pazopanib 1 HCl, as determined by XRPD. The lyophilized salt is dissolved in the solution at a temperature between about 37° C. to about 50° C. The lyophilizing from an organosulfur compound converts crystalline phase Form A of pazopanib 1 HCl to a material containing at least about 70% Form G of pazopanib 1 HCl, as determined by XRPD. The lyophilizing from dimethyl sulfoxide (DMSO) converts crystalline phase Form A of pazopanib 1 HCl to a material containing up to or at least about 70% Form G of pazopanib 1 HCl, as determined by XRPD. The lyophilizing from dimethyl sulfoxide (DMSO) converts crystalline phase Form A of pazopanib 1 HCl to a material containing about 100% Form G of pazopanib 1 HCl, as determined by XRPD. The lyophilized salt is dissolved in the solution at a temperature between about 37° C. to about 50° C. The present disclosure provides a method of converting a crystal form of pazopanib to a material containing crystal Form G of pazopanib, the method comprising dissolving the crystal form in DMSO and lyophilizing the resulting solution; wherein at least about 70% Form G of pazopanib is formed.

The present disclosure provides a method of converting crystal Form A of pazopanib to a material containing crystal Form G of pazopanib, the method comprising dissolving Form A in DMSO and lyophilizing the resulting solution; wherein the up to or at least about 70% Form G of pazopanib is formed. The present disclosure provides a method of converting crystal Form A of pazopanib to a material containing crystal Form G of pazopanib, the method comprising dissolving the crystal Form A in DMSO and lyophilizing the resulting solution; in which between about 70% to about 100% (e.g., about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%) Form G of pazopanib is formed.

The methods of converting a crystal form (e.g., Form A) of pazopanib to a material containing crystal Form G provide up to about 50%, up to about 51%, up to about 52%, up to about 53%, up to about 54%, up to about 55%, up to about 56%, up to about 57%, up to about 58%, up to about 59%, up to about 60%, up to about 61%, up to about 62%, up to about 63%, up to about 64%, up to about 65%, up to about 66%, up to about 67%, up to about 68%, up to about 69%, or up to about 70% Form G is of pazopanib is formed. Alternatively, the methods provide that at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% Form G of pazopanib is formed.

The present disclosure provides a crystalline form of a therapeutic agent, e.g., pazopanib monohydrochloride, pretreated prior to formulation process. The crystalline form of the therapeutic agent, e.g., pazopanib monohydrochloride, is pretreated by lyophilization (see Table 4 for an example of the lyophilization conditions from DMSO). About 20-60 mg/mL of a therapeutic agent, e.g., pazopanib monohydrochloride, solution in DMSO (dimethyl sulfoxide) is prepared. The solution is then freeze dried under standard condition in the art. Drying conditions of the present disclosure are at temperature higher than ambient temperature. For example, the solutions of the present disclosure are dried under about 35° C.-about 50° C. (e.g., about 40° C.) for about 12-about 24 hours and about 50° C.-about 65° C. (e.g., at about 60° C.) for about 24-about 40 hours and at about 90-about 110° C. (e.g., at about 100° C.) for about 0.5-about 2 hours. The lyophilization from DMSO converts crystalline phase Form A to crystalline phase Form G, as determined by XRPD.

The lyophilizing step from DMSO in the method of the present disclosure converts a crystalline phase Form A of pazopanib, having XRPD peaks at 5.6, 15.5, 16.4, 24.0 and 24.3±0.2 degrees at 2θ (further characterized by peaks at 10.5, 16.8, 17.9, 26.4 and 32.9±0.2 degrees at 2θ), to Form G, characterized by XRPD peaks at 9.6, 16.8, 19.6, 24.7 and 26.2±0.2 degrees at 2θ (further characterized by peaks at 11.8, 14.6, 15.3, 18.4, 20.3 and 23.6±0.2 degrees at 2θ).

The present disclosure provides a method of preparing a stable pharmaceutical formulation of a pharmaceutically acceptable monovalent salt of a therapeutic agent, including the steps of: (a) preparing a solution of the salt in an organic solvent (TFE or DMSO); and (b) lyophilizing the solution, thereby preparing a lyophilized salt of the therapeutic agent. The method of preparing a stable pharmaceutical formulation of a pharmaceutically acceptable monovalent salt of a therapeutic agent further includes the steps of: (c) dissolving a solubilizing agent and a buffering agent in water, thereby preparing a solution; (d) dissolving a complexing agent in the aqueous solution of the solubilizing agent and the buffering agent, thereby preparing a solution; (e) adding the lyophlilized salt to the solution, mixing, dissolving in the solution at equal to or higher (about 37° C.-about 50° C.) than about ambient temperature; and (f) optionally adjusting the pH of the formulation. The lyophilized salt is dissolved in the solution at a temperature between about 37° C. to about 50° C. (e.g., at about 37° C., at about 38° C., at about 39° C., at about 40° C., at about 41° C., at about 42° C., at about 43° C., at about 44° C., at about 45° C., at about 46° C., at about 47° C., at about 48° C., at about 49° C., at about 50° C.).

The solubilizing agent used in the method is PVP. The buffering agent used in the method is Histidine HCl. The complexing agent used in the method is a cyclodextrin is: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof.

The present disclosure provides a method of preparing a stable pharmaceutical formulation of a pharmaceutically acceptable monovalent salt of pazopanib, e.g., a monovalent chloride salt of pazopanib, a monovalent bromide salt of pazopanib, a monovalent iodide salt of pazopanib, or a monovalent fluoride salt of pazopanib, including the steps of: (a) preparing a solution of the salt in an organic solvent (TFE or DMSO); and (b) lyophilizing the solution, thereby preparing a lyophilized salt of pazopanib. The method of preparing a stable pharmaceutical formulation of a pharmaceutically acceptable monovalent salt of pazopanib provides that after lyophilization, the lyophilized monovalent halide salt of pazopanib, e.g., a monovalent chloride salt, e.g., hydrochloride salt, of pazopanib, a monovalent bromide salt of pazopanib, a monovalent iodide salt of pazopanib, or a monovalent fluoride salt of pazopanib, is amorphous.

The method of preparing a stable and in solution pharmaceutical formulation of a pharmaceutically acceptable monovalent salt of pazopanib further involves: (c) dissolving a solubilizing agent and a buffering agent in water, thereby preparing a solution; (d) dissolving a complexing agent in the aqueous solution of the solubilizing agent and the buffering agent, thereby preparing a solution; (e) adding the lyophlilized salt to the viscous solution, mixing, dissolving in the solution at equal to or higher (e.g., about 37° C. or 50° C.) than about ambient temperature; and (f) optionally adjusting the pH of the formulation. The lyophilized salt is dissolved in the solution at a temperature between about 37° C. to about 50° C. (e.g., at about 37° C., at about 38° C., at about 39° C., at about 40° C., at about 41° C., at about 42° C., at about 43° C., at about 44° C., at about 45° C., at about 46° C., at about 47° C., at about 48° C., at about 49° C., at about 50° C.).

The solubilizing agent used in the method of preparing a formulation of monovalent pazopanib is PVP. The buffering agent used in the same method is Histidine HCl. The complexing agent used in the same method is a cyclodextrin is: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof.

The method of preparing a stable and in solution pharmaceutical formulation of a pharmaceutically acceptable monovalent salt of pazopanib provides a stable formulation of a monovalent halide salt of pazopanib, e.g., a monovalent chloride salt of pazopanib, a monovalent bromide salt of pazopanib, a monovalent iodide salt of pazopanib, or a monovalent fluoride salt of pazopanib. The method of preparing a stable pharmaceutical formulation of a pharmaceutically acceptable monovalent salt of pazopanib provides a stable formulation of a monovalent chloride salt of pazopanib.

The present disclosure provides a method in which native pH of the formulation is used, i.e. no pH adjustment of viscous solution is necessary. In this method, solubilization of the pharmaceutical ingredient is performed in one step. PVP-10k (polyvinyl pyrrolidone, MW=10 kDa) and Histidine HCl are weighed and dissolved in the appropriate amount of water by mixing the solution (vortex, shaking). CAPTISOL® is weighed, added and dissolved in the solution with shaking, vortexing the solution. Lyophilized pazopanib is weighed and then added to the viscous CAPTISOL® solution and dissolved completely by vortex, sonication, shaking at ambient or at elevated (about 37° C.-about 50° C.) temperatures. The formulation is filtered using a 0.2 µm filter and stored at room temperature and protected from light.

The present disclosure provides a method of preparing a stable, solution pharmaceutical formulation of a pharmaceutically acceptable salt of a therapeutic agent having low aqueous solubility, in which the salt is a monovalent salt, e.g., pazopanib 1 HCl; the method includes (a) preparing a solution of the salt in an organic solvent (e.g., trifluoro ethanol, trifluoro ethanol-water mixture, or dimethyl sulfoxide); (b) lyophilizing the solution, thereby preparing a lyophilized salt of the therapeutic agent; (c) dissolving a solubilizing agent and a buffering agent in water, thereby preparing a solution; dissolving an amount of a complexing agent in the solution, thereby preparing a low viscosity solution; adding a lyophilized salt to the low viscosity solution, mixing, dissolving in the solution at equal to or higher (about 37° C.-about 50° C.) than about ambient temperature; wherein pH of the low viscosity solution is adjusted; and adding and dissolving about 2× more the amount of the complexing agent to the low viscosity solution. The lyophilized salt is dissolved in the solution at a temperature between about 37° C. to about 50° C. (e.g., at about 37° C., at about 38° C., at about 39° C., at about 40° C., at about 41° C., at about 42° C., at about 43° C., at about 44° C., at about 45° C., at about 46° C., at about 47° C., at about 48° C., at about 49° C., at about 50° C.).

The present disclosure provides methods of preparing formulations of a therapeutic agent in which CAPTISOL® is added in two steps in order to reduce the viscosity of the solution during the formulation preparation process. The method comprises, e.g., preparing an aqueous solution of CAPTISOL®, using half of the total CAPTISOL® amount; dissolving the therapeutic agent and additives (e.g., PVP, Histidine), adjust the pH of the formulation, and then adding the remaining amount of CAPTISOL®. The two step process produces a lower viscosity solution which affords a faster dissolution and ease in pH measurement than with a high viscosity solution.

The formulation further comprises a buffering agent (e.g., an organic buffer, e.g., Histidine or Histidine HCl) and a pH adjusting agent (e.g., an inorganic base, e.g., NaOH; an organic base, e.g., megalumine; or an organic buffer, e.g., Histidine or Histidine HCl). In some embodiment, the pH of the formulation of a therapeutic agent, e.g., Pazopanib, is adjusted with an inorganic base, e.g., NaOH. In other embodiments, the pH of the formulation of a therapeutic agent, e.g., pazopanib, is adjusted with an organic base, e.g., meglumine. In some embodiments, the present disclosure provides a non-precipitating formulation of a therapeutic agent, e.g., pazopanib, in which an organic base, e.g., Meglumine is used. In some embodiments, additional additives (e.g., triacetin, glycerol) are added for increasing the stability (against precipitation) of the formulations.

The present disclosure provides a method of preparing stable and in solution formulation of a monovalent salt, e.g., monovalent hydrochloride salt, of a therapeutic agent, e.g., pazopanib, by first weighing and dissolving approximately half of required CAPTISOL® in a vial containing an appropriate amount of water. PVP-10k (polyvinyl pyrrolidone, MW=10 kDa) and Histidine HCl are added and dissolved in the solution by mixing the solution (vortex, sonication, shaking). Lyophilized pazopanib is weighed and then added to the CAPTISOL® solution. If needed, small amount of hydrochloric acid (HCl) is added to adjust and maintain the pH of the solution at equal to or lower than about pH=2. Additives such as triacetin or glycerol are added. The formulation is stirred and shaken at 37° C. or at room temperature until pazopanib is completely dissolved. The dissolution of pazopanib can take several hours. Next, the pH of the pazopanib-CAPTISOL® solution is adjusted to about pH 6-7 by adding NaOH or Meglumine. Remaining CAPTISOL® is then added and dissolved completely by shaking/vortex the formulation at 37° C. or at room temperature. The pH is checked and, if needed, adjusted, before filtering the formulation using a 0.2 µm filter. The formulation is stored at room temperature and protected from light. Content and purity of the formulation is tested by HPLC and UV.

The present disclosure provides a formulation method in which all solid excipients (CAPTISOL®, PVP and Histidine-HCl) and the therapeutic agent (e.g., lyophilized pazopanib 1 HCl) are measured and mixed together first in a vial. Using continuous mixing, gradual addition of the required water is performed. The solubilization of the formed dispersion can be done at ambient or elevated temperatures (e.g., about 37° C. or about 50° C.); using elevated temperatures reduces the time needed to achieve homogeneous solutions (e.g., about 24 hours to about 4 hours). The formulation is then used under native pH about 3-about 4, or is used after pH adjustment with NaOH solution (pH about 6-about 7).

The present disclosure provides a method in which at least a solubilizing agent, a buffering agent, a complexing agent, and the lyophilized salt are continuously mixed, while adding water, at equal to or higher than about ambient temperature. The pH of the formulation is adjusted to about 6-7 with a base.

The present disclosure provides a method in which at least a solubilizing agent, a buffering agent, a complexing agent, and the lyophilized monohydrochloride salt of pazopanib are continuously mixed, while adding water, at equal to or higher than about ambient temperature. The pH of the formulation is adjusted to about 6-7 with a base. The complexing agent in the method is a cyclodextrin is: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof; the solubilizing agent is poly(vinyl pyrrolidone) (PVP); and the buffering agent is Histidine HCl.

The present disclosure provides a method in which at least a solubilizing agent, a buffering agent, a complexing agent, and the lyophilized monohydrochloride salt of pazopanib are continuously mixed, while adding water, at equal to or higher than about ambient temperature. In this method, the pH of the formulation is not adjusted. The complexing agent in the method is a cyclodextrin is: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or any combination(s) thereof; the solubilizing agent is poly(vinyl pyrrolidone) (PVP); and the buffering agent is Histidine HCl.

Release Rate of Therapeutic Agents

The present disclosure provides therapeutic agent release rate measured by the amount of therapeutic agent released by a PDS into receiver fluid (PBS buffer) at 37° C. Therapeutic agent release testing is performed by measuring the amount of therapeutic agent released by the PDS into a fluid representative of vitreous, maintained at 37° C. in an incubator. The PDS is suspended in a container containing phosphate buffered saline. Periodically, the PDS is transferred into a new container and the concentration of therapeutic agent is measured in the fluid of the previous container. Rates are calculated from the amount of therapeutic agent released divided by the sample collection duration. The percent cumulative release is calculated from the cumulative amount of therapeutic agent divided by the amount of therapeutic agent initially filled into the therapeutic device (PDS). The half-life is calculated from the percent cumulative release at 4 weeks. The present disclosure provides conditions upon release of a small amount of formulation into a large amount of buffer solution. If the drug precipitates out upon dilution (release) that can cause clogging of the delivery device and/or loss of drug because the solid drug will not be measurable in the receiver fluid. Moreover, the precipitation prevents the efficacious treatment with the active because the drug is inaccessible in vivo.

The present disclosure provides conditions for testing drug precipitation in which the formulation, e.g., is diluted 330 fold with phosphate buffered saline solution (with, e.g., 0.1% sodium azide), e.g., about 3 µL of formulation is added to 1 mL PBS buffer. The solution is kept in a thermostat (temperature, e.g., 37° C.) and periodically checked for appearance of crystal growth/precipitation. The present disclosure provides that the formulations prepared with different drug samples (sample-1 or 2 of pazopanib HCl) exhibits different stability against precipitation upon dilution.

TABLE 5

| Formulation* | Drug/treatment | Time (approximate in days) till precipitation was observed (in 330x dilution) |
|---|---|---|
| 60 mg/mL, 660 mg/mL CAPTISOL ®, 1% PVP-10 kD, 6 mg/mL Histidine HCl, pH 6 ('PA96') | Pazopanib-2HCl | Not tested; no precipitation during drug release |
| 62 mg/mL, 660 mg/mL CAPTISOL ®, 1% PVP-10 kD, 6 mg/mL Histidine HCl, pH 6 ('PA110') | Pazopanib-1HCl | Less than 5 days |
| 60 mg/mL, 660 mg/mL CAPTISOL ®, 1% PVP-10 kD, 6 mg/mL Histidine HCl, pH 6 ('PA96') | Pazopanib-1HCl-lyophilized-DMSO | 14 days |
| 40 mg/mL, 660 mg/mL CAPTISOL ®, 1% PVP-10 kD, 6 mg/mL Histidine HCl, pH 6 ('PA139') | Pazopanib-1HCl | 13 days |
| 41 mg/mL, 660 mg/mL CAPTISOL ®, 1% PVP-10 kD, 6 mg/mL Histidine HCl, pH 7 ('PAL11') | Pazopanib-1HCl-lyophilized-TFE | 41 days |
| 45 mg/mL, 660 mg/mL CAPTISOL ®, 1% PVP-10 kD, 6 mg/mL Histidine HCl, pH 3.5 ('PAD7') | Pazopanib-1HCl-lyophilized-DMSO | 1 year (approximately) |

*Drug concentration is for pazopanib salt, mg/mL

The release rate of the therapeutic agent of the current disclosure in a formulation of about 1 mg/mL to about 100 mg/mL under various fill concentrations varies between about 100 µg/mL on day 1, to about 0.01 µg/mL on day 140. The present disclosure provides that the release rate is a function of HCl content and/or crystalline form of a pharmaceutically acceptable salt of pazopanib. Compared to the release rate of pazopanib 1 HCl, the release rate of pazopanib 2 HCl is higher and sustainable for more than 100 days.

Lyophilization is believed to transfer the highly crystalline drug to mostly amorphous solid, which has more favorable solubility properties. As shown in FIG. 1, formulations prepared from lyophilized 1 HCl salt pazopanib active agent have significantly improved stability (against precipitation/crystallization) compared to the highly crystalline 1 HCl form, and also resulted in comparable drug release characteristics to the 2 HCl form.

The present disclosure provides that the release rate between about 12 µg/day on day 1 to about 1-about 3 µg/day, on around or more than about 20 days, of un-lyophilized pazopanib 1 HCl (sample-2) from a formulation of CAPTISOL®, a solubilizing agent, e.g., PVP, and a buffering agent, e.g., Histidine HCl, and pH of the formulation adjusted to about 6.5. The half-life of the drug release is about 99 days. Moreover, un-lyophilized pazopanib 1 HCl precipitates off the solution during drug release. The un-lyophilized pazopanib 1 HCl (sample-2) in the formulation is about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 53 mg/mL, about 54 mg/mL, about 55 mg/mL, about 56 mg/mL, about 57 mg/mL, about 58 mg/mL, about 59 mg/mL, about 60.0 mg/mL, about 61 mg/mL, about 62 mg/mL, about 63 mg/mL, about 64 mg/mL, about 64 mg/mL, or about 65 mg/mL. The ratio of CAPTISOL®:pazopanib 1 HCl in the formulation is about 9:1, about 8:1, about 7:1, about 6:1, about 5:1, about 4:1, about 3:1, or about 2:1. For example, the CD:pazopanib 1 HCl ratio is about 2.2:1; about 2.5:1; about 3.7:1; about 5:1; about 8:1; or about 9:1. For example, the ratio of CD:pazopanib 1 HCl is about 2.5:1 or 2.2:1.

The present disclosure provides a stable formulation with about 60 mg/mL pazopanib 2 HCl, about 660 mg/mL CAPTISOL®, about 1% PVP-10kD, about 6 mg/mL Histidine HCl, about pH 6, such that the pazopanib 2 HCl does not precipitate during ambient storage for up to a year and does not or only minimally precipitate upon dilution within at least 40-120 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) at least 40-120 days. Pazopanib 1 HCl in the present formulation does not or minimally precipitate during and/or after release from a drug delivery device of the present disclosure into a body part, e.g., vitreous of the eye, within at least 40-120 days.

The present disclosure provides that the release rate between about 20 µg/day on day 1 to about 2-about 4 µg/day, on around or more than about 140 days, of pazopanib 2 HCl (sample-1) from a formulation of CAPTISOL®, a solubilizing agent, e.g., PVP, and a buffering agent, e.g., Histidine HCl, and pH of the formulation adjusted to about 6.5. The half-life of the drug release is about 53 days. Pazopanib 2 HCl (sample-1) in the formulation is about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 53 mg/mL, about 54 mg/mL, about 55 mg/mL, about 56 mg/mL, about 57 mg/mL, about 58 mg/mL, about 59 mg/mL, about 60.0 mg/mL, about 61 mg/mL, about 62 mg/mL, about 63 mg/mL, about 64 mg/mL, about 64 mg/mL, or about 65 mg/mL. The ratio of CAPTISOL®:pazopanib 2 HCl in the formulation is about 9:1, about 8:1, about 7:1, about 6:1, about 5:1, about 4:1, about 3:1, or about 2:1. For example, the CD:pazopanib 2 HCl ratio is about 2.2:1; about 2.5:1; about 3.7:1; about 5:1; about 8:1; or about 9:1. For example, the ratio of CD:pazopanib 2 HCl is about 2.5:1 or 2.2:1.

The present disclosure provides a stable formulation with about 62 mg/mL pazopanib 1 HCl, about 660 mg/mL CAPTISOL®, about 1% PVP-10kD, about 6 mg/mL Histidine HCl, about pH 6, such that the pazopanib 1 HCl does not precipitate during ambient storage for up to 9 months and does not or minimally precipitate when diluted within 5-10 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) within 5-10 days. Pazopanib 1 HCl in the present formulation does not or minimally precipitate during and/or after release from a drug delivery device of the present disclosure into a body part, e.g., vitreous of the eye, within 5-10 days.

The present disclosure provides a stable formulation with about 40 mg/mL pazopanib 1 HCl, about 660 mg/mL CAPTISOL®, about 1% PVP-10kD, about 6 mg/mL Histidine HCl, about pH 6, such that the pazopanib 1 HCl does not precipitate during ambient storage for up to at least 9 months and does not or minimally precipitate when diluted within at least 13-20 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) within at least 13-20 days. Pazopanib 1 HCl in the present formulation does not or minimally precipitate during and/or after release from a drug delivery device of the present disclosure into a body part, e.g., vitreous of the eye, within at least 13-20 days.

The present disclosure provides that the release rate between about 12 µg/day on day 1 to about 1-about 2 µg/day, on around or more than about 140 days, of TFE lyophilized pazopanib 1 HCl (sample-2) from a formulation of CAPTISOL®, a solubilizing agent, e.g., PVP, and a buffering agent, e.g., Histidine HCl, and pH of the formulation adjusted to about 6.5. The half-life of the drug release is about 45 days. Pazopanib 2 HCl (sample-1) in the formulation is about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 53 mg/mL, about 54 mg/mL, about 55 mg/mL, about 56 mg/mL, about 57 mg/mL, about 58 mg/mL, about 59 mg/mL, about 60.0 mg/mL, about 61 mg/mL, about 62 mg/mL, about 63 mg/mL, about 64 mg/mL, about 64 mg/mL, or about 65 mg/mL. The ratio of CAPTISOL®:pazopanib 2 HCl in the formulation is about 9:1, about 8:1, about 7:1, about 6:1, about 5:1, about 4:1, about 3:1, or about 2:1. For example, the CD:pazopanib 2 HCl ratio is about 2.2:1; about 2.5:1; about 3.7:1; about 5:1; about 8:1; or about 9:1. For example, the ratio of CD:pazopanib 2 HCl is about 4:1. The PVP in the formulation is about 1%, and Histidine HCl in the formulation is about 25 mg/mL.

The present disclosure provides that the release rate of between about 12 µg/day on day 1 to about 1-about 2 µg/day, on around or more than about 140 days from a formulation of about 36.0 mg/mL TFE lyophilized pazopanib 1 HCl (sample-2) from a formulation in which CAPTISOL® is present in a ratio of CAPTISOL®:pazopanib of about 4:1, and in the presence of a solubilizing agent, e.g., about 1% PVP, and a buffering agent, e.g., about 25 mg/ml Histidine HCl, and pH of the formulation adjusted to about 6.5. The half-life of the drug release is about 45 days.

The present disclosure provides a stable formulation with about 41 mg/mL pazopanib 1 HCl lyophilized from TFE, about 660 mg/mL CAPTISOL®, about 1% PVP-10kD, about 6 mg/mL Histidine HCl, about pH 7, such that the pazopanib 1 HCl does not precipitate during ambient storage within up to 6 months and does not or minimally precipitate when diluted within at least 41-120 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) within at least 41-120 days. Pazopanib 1 HCl in the present formulation does not or minimally precipitate during and/or after release from a drug delivery device of the present disclosure into a body part, e.g., vitreous of the eye, within at least 41-120 days.

The present disclosure provides that the release rate between about 16 µg/day on day 1 to about 1-about 3 µg/day, on around or more than about 140 days, of DMSO lyophilized pazopanib 1 HCl (sample-2) from a formulation of CAPTISOL®, a solubilizing agent, e.g., PVP, and a buffering agent, e.g., Histidine HCl, and pH of the formulation adjusted to about 3.4. The half-life of the drug release is about 45 days. Pazopanib 2 HCl (sample-1) in the formulation is about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 53 mg/mL, about 54 mg/mL, about 55 mg/mL, about 56 mg/mL, about 57 mg/mL, about 58 mg/mL, about 59 mg/mL, about 60.0 mg/mL, about 61 mg/mL, about 62 mg/mL, about 63 mg/mL, about 64 mg/mL, about 64 mg/mL, or about 65 mg/mL. The ratio of CAPTISOL®:pazopanib 2 HCl in the formulation is about 9:1, about 8:1, about 7:1, about 6:1, about 5:1, about 4:1, about 3:1, or about 2:1. For example, the CD:pazopanib 2 HCl ratio is about 2.2:1; about 2.5:1; about 3.7:1; about 5:1; about 8:1; or about 9:1. For example, the ratio of CD:pazopanib 2 HCl is about 3:1. The PVP in the formulation is about 1%, and Histidine HCl in the formulation is about 6 mg/mL.

The present disclosure provides a stable formulation with about 60 mg/mL pazopanib 1 HCl lyophilized from DMSO, about 660 mg/mL CAPTISOL®, about 1% PVP-10kD, optionally about 6 mg/mL Histidine HCl, about pH 6, such that the pazopanib 1 HCl does not precipitate during ambient storage within up to 40 days and does not or minimally precipitate when diluted within at least 10-14 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) within at least 10-14 days. Pazopanib 1 HCl in the present formulation does not or minimally precipitate during and/or after release from a drug delivery device of the present disclosure into a body part, e.g., vitreous of the eye, within at least 10-14 days.

The present disclosure provides a stable formulation with about 45 mg/mL pazopanib 1 HCl lyophilized from DMSO, about 660 mg/mL CAPTISOL®, about 1% PVP-10kD, about 6 mg/mL Histidine HCl, about pH 3.5, such that the pazopanib 1 HCl does not precipitate during storage at ambient temperature and does not or minimally precipitate when diluted within at least 50 days. Pazopanib 1 HCl in the present formulation does not or minimally precipitate upon dilution up to about 350-folds (e.g., about 50-100-folds, about 100-150-folds, about 150-200-folds, about 200-250-folds, about 250-300-folds, about 300-310-folds, about 310-320-folds, about 320-330-folds, about 330-340-folds, or about 340-350-folds) at between about 30° C.-about 50° C. (e.g., about 37° C.) within at least 50 days. Pazopanib 1 HCl in the present formulation does not or minimally precipitate during and/or after release from a drug delivery device of the present disclosure into a body part, e.g., vitreous of the eye, within at least 50 days.

The present disclosure provides that the release rate of about 50.0 mg/mL DMSO lyophilized pazopanib 1 HCl (sample-2) from a formulation in which CAPTISOL® is present in a ratio of CAPTISOL®:pazopanib of about 3:1, and in the presence of a solubilizing agent, e.g., about 1% PVP, and a buffering agent, e.g., about 6 mg/ml Histidine HCl, and pH of the formulation adjusted to about 3.4, is between about 16 µg/day on day 1 to about 1-about 3 µg/day, on around or more than about 140 days. The half-life of the drug release is about 45 days.

The present disclosure provides release rate of pazopanib formulations from a delivery device wherein the formulation is prepared without a buffering agent, and includes pazopanib 1 HCl (between about 30 mg/mL to about 40 mg/mL), about 660-about 700 mg/mL (e.g., about 660 mg/mL) CAPTISOL®, polymer (e.g., PVP), and with native pH. The fill concentration is about 30 mg/mL-about 35 mg/mL (large scale lyophilized formulation) or about 35 mg/mL-about 45 mg/mL (small scale lyophilized formulation). Table 6 provides non-limiting examples of the release rate of the formulations of the present disclosure.

TABLE 6

Time-point for RRI (days) 3

| Formulation | | Fill Conc. (about mg/mL) | D (cm$^2$/s) | RRI (mm) |
|---|---|---|---|---|
| PAD-20 2.5 sccm | Pazopanib HCl, about 33 mg/mL, FBE-Lyo; about 660 mg/mL CAPTISOL® (4x); about 1% PVP; No Histidine HCl; about 50° C., for 6 hours -pH native | 37.00 | 4.90E−06 | 0.0056 |
| PAD-20 4.5 sccm | Pazopanib HCl, about 33 mg/mL, FBE-Lyo; about 660 mg/mL CAPTISOL® (4x); 1% PVP; No Histidine HCl; about 50° C., for 6 hours -pH native | 37.00 | 4.90E−06 | 0.0069 |
| PAD-21 2.5 sccm | Pazopanib HCl, about 33 mg/mL FBE-Lyo; 660 mg/mL CAPTISOL® (4x); about 1% PVP; No Histidine HCl; about 50° C., for 6 hours -pH native | 40.08 | 4.90E−06 | 0.0050 |
| PAD-21 4.5 sccm | Pazopanib HCl, about 33 mg/mL FBE-Lyo; about 660 mg/mL CAPTISOL® (4x); about 1% PVP; No Histidine-HCl; about 50° C., for 6 hours -pH native | 40.08 | 4.90E−06 | 0.0067 |

Kit

The present disclosure provide a kit in which any one of the stable formulations of the present disclosure is contained in a reservoir chamber of a therapeutic device, wherein the reservoir chamber is coupled to a porous structure for controlled release of the therapeutic agent in the vitreous of the eye.

Therapeutic Device

The therapeutic device includes many configurations and physical attributes, for example the physical characteristics of the therapeutic device comprise at least one of a therapeutic agent delivery device (Port Delivery System (PDS)) with a suture, positioning and sizing such that vision is not impaired, and biocompatible material. For example, the device comprises a reservoir capacity from about 0.005 cc to about 0.2 cc, for example from about 0.01 cc to about 0.1 cc, and a device volume of no more than about 2 cc. A vitrectomy is performed for device volumes larger than 0.1 cc. The length of the therapeutic device does not interfere with the patient's vision and is dependent on the shape of the device, as well as the location of the implanted device with respect to the eye. The length of the device also depends on the angle in which the device is inserted. For example, a length of the device comprises from about 4 to 6 mm. Since the diameter of the eye is about 24 mm, a device extending no more than about 6 mm from the sclera into the vitreous has a minimal effect on patient vision.

Variations comprise many combinations of implanted therapeutic agent delivery devices (Port Delivery System (PDS)). The therapeutic device comprises a therapeutic agent and binding agent. The device also comprises at least one of a membrane, an opening, a diffusion barrier, a diffusion mechanism so as to release therapeutic amounts of therapeutic agent for the extended time. Several variations of the device have been disclosed in WO 2012/065006, WO2012/019047, WO2013/003620, WO 2012/019136, WO 2012/019176, and U.S. Pat. No. 8,277,830, each of which is incorporated by reference herein in its entirety.

Figure 2A:
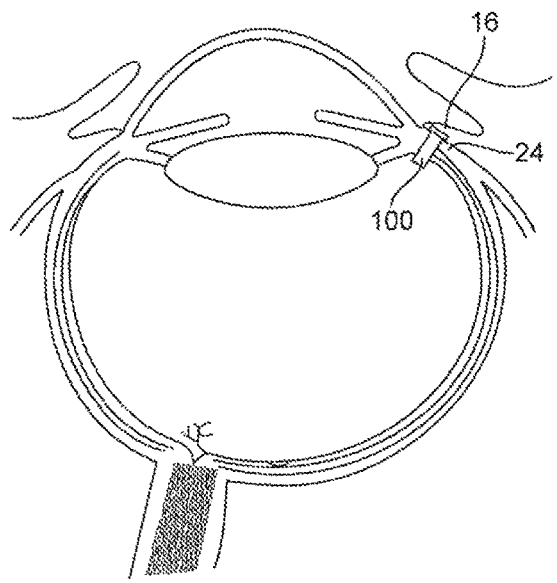
FIG. 2A shows a therapeutic device implanted under the conjunctiva and extending through the sclera to release a therapeutic agent into vitreous humor of the eye so as to treat the retina, in accordance with variations described herein.

FIG. 2A shows a therapeutic device 100 implanted under the conjunctiva 16 and extending through the sclera 24 to release a therapeutic agent into vitreous humor of the eye so as to treat the retina of the eye. The therapeutic device 100 includes a retention structure 120 such as a smooth protrusion configured for placement along the sclera and under the conjunctiva, such that the conjunctiva covers the therapeutic device and protects the therapeutic device 100. When the therapeutic agent 110 is inserted into the device 100, the conjunctiva is lifted away, incised, or punctured with a needle to access the therapeutic device. The eye includes an insertion of the tendon 27 of the superior rectus muscle to couple the sclera of the eye to the superior rectus muscle. In embodiments, the device 100 is positioned in many locations of the pars plana region, for example away from tendon and one or more of posterior to the tendon, under the tendon, or with nasal or temporal placement of the therapeutic device.

While the implant can be positioned in the eye in many ways, work in relation to variations suggests that placement in the pars plana region releases therapeutic agent into the vitreous to treat the retina, for example therapeutic agent comprising an active ingredient composed of large molecules.

Therapeutic agents 110 suitable for use with device 100 include many therapeutic agents, for example as listed in Table 1. The therapeutic agent 110 of device 100 includes one or more of an active ingredient of the therapeutic agent, a formulation of the therapeutic agent, components of a formulation of the therapeutic agent, a physician prepared formulation of therapeutic agent, or a pharmacist prepared formulation of the therapeutic agent.

The therapeutic device 100 can be implanted in the eye to treat the eye for as long as is helpful and beneficial to the patient. For example, the device is implanted for at least about 5 years, such as permanently for the life of the patient. Alternatively or in combination, the device is removed when no longer helpful or beneficial for treatment of the patient.

Figure 2B:
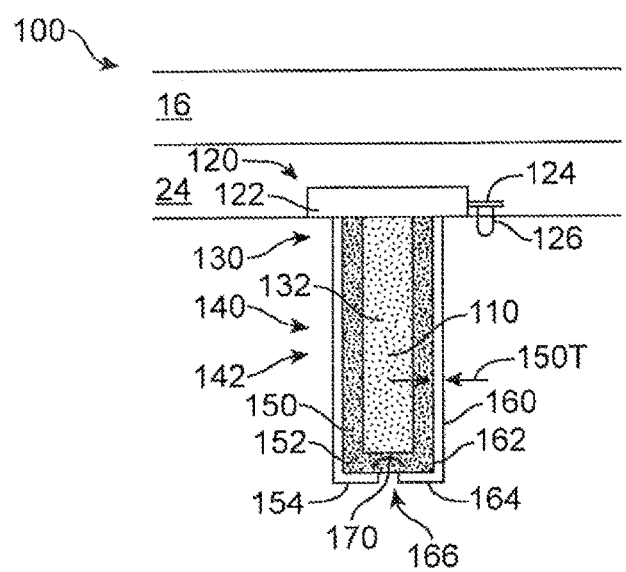
FIG. 2B shows structures of a therapeutic device configured for placement in an eye as in FIG. 2A, in accordance with variations described herein.

FIG. 2B shows structures of therapeutic device 100 configured for placement in an eye as in FIG. 2A. The device comprises retention structure 120 to couple the device 100 to the sclera, for example a protrusion disposed on a proximal end of the device. The device 100 comprises a container 130 affixed to the retention structure 120. An active ingredient, for example therapeutic agent 110, is contained within a reservoir 140, for example a chamber 132 defined by a container 130 of the device. The container 130 includes a porous structure 150 comprising a porous material 152, for example a porous glass frit 154, and a barrier 160 to inhibit release of the therapeutic agent, for example non-permeable membrane 162. The non-permeable membrane 162 comprises a substantially non-permeable material 164. The non-permeable membrane 162 includes an opening 166 sized to release therapeutic amounts of the therapeutic agent 110 for the extended time. The porous structure 150 includes a thickness 150T and pore sizes configured in conjunction with the opening 166 so as to release therapeutic amounts of the therapeutic agent for the extended time. The container 130 includes reservoir 140 having a chamber with a volume 142 sized to contain a therapeutic quantity of the therapeutic agent 110 for release over the extended time. The device includes a needle stop 170. Proteins in the vitreous humor enter the device and compete for adsorption sites on the porous structure and thereby contribute to the release of therapeutic agent. The therapeutic agent 110 contained in the reservoir 140 equilibrate with proteins in the vitreous humor, such that the system is driven towards equilibrium and the therapeutic agent 110 is released in therapeutic amounts.

The non-permeable material such as the non-permeable membrane 162, the porous material 152, the reservoir 140, and the retention structure 120, comprise many configurations to deliver the therapeutic agent 110. The non-permeable membrane 162 comprises an annular tube joined by a disc having at least one opening formed thereon to release the therapeutic agent. The porous material 152 comprises an annular porous glass frit 154 and a circular end disposed thereon. The reservoir 140 is shape-changing for ease of insertion; i.e., it assumes a thin elongated shape during insertion through the sclera and then assumes an extended, ballooned shape, once it is filled with therapeutic agent.

The porous structure 150 can be configured in many ways to release the therapeutic agent in accordance with an intended release profile. The porous structure comprises a single hole or a plurality of holes extending through a barrier material such as a rigid plastic or a metal. Alternatively or in combination, the porous structure comprises a porous structure having a plurality of openings on a first side facing the reservoir and a plurality of openings on a second side facing the vitreous humor, with a plurality of interconnecting channels disposed there between so as to couple the openings of the first side with the openings of the second side, for example a sintered rigid material. The porous structure 150 comprises one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

Figure 2C:
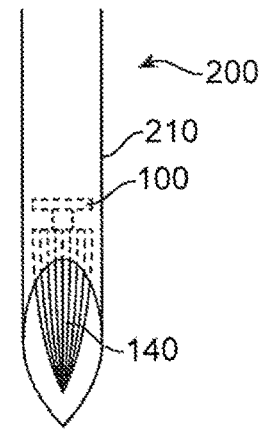
FIG. 2C shows a therapeutic device loaded into an insertion cannula, in which the device comprises an elongate narrow shape for insertion into the sclera, and in which the device is configured to expand to a second elongate wide shape for retention at least partially in the sclera, in accordance with variations described herein.

FIG. 2C shows therapeutic device 100 loaded into an insertion cannula 210 of an insertion apparatus 200, in which the device 100 comprises an elongate narrow shape for insertion into the sclera, and in which the device is configured to expand to a second elongate wide shape for retention at least partially in the sclera.

Figure 2D:
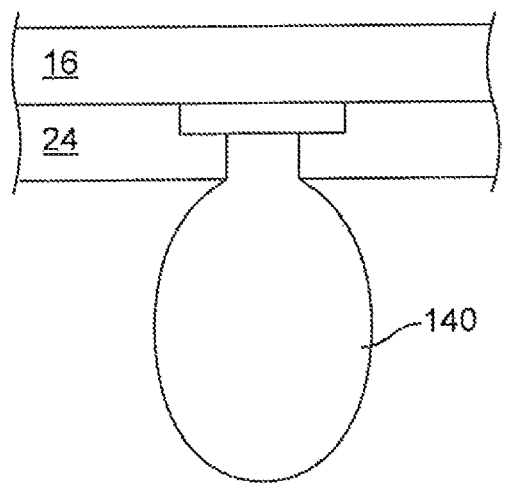
FIG. 2D shows a therapeutic device comprising a reservoir suitable for loading in a cannula, in accordance with variations described herein.

FIG. 2D shows a therapeutic device 100 comprising reservoir 140 suitable for loading in a cannula, in which the reservoir 140 comprises an expanded configuration when placed in the eye.

Figure 2E:
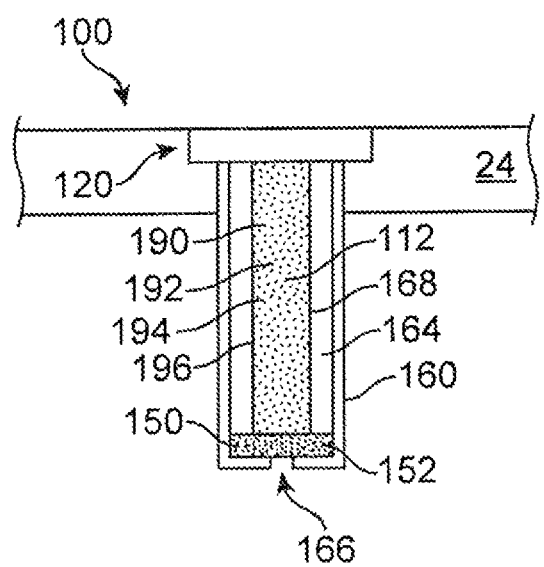
FIG. 2E shows a therapeutic device configured for placement in an eye as in FIG. 2A, in accordance with variations described herein.

FIG. 2E shows therapeutic device 100 placed in an eye as in FIG. 2A. The device comprises retention structure 120 to couple to the sclera, for example flush with the sclera, and the barrier 160 comprises a tube 168. An active ingredient 112 comprising the therapeutic agent 110 is contained within tube 168 comprising non-permeable material 164. A porous structure 150 comprising a porous material 152 is disposed at the distal end of the tube 168 to provide a sustained release of the therapeutic agent at therapeutic concentrations for the extended period. The non-permeable material 164 extends distally around the porous material 152 so as to define an opening to couple the porous material 152 to the vitreous humor when the device is inserted into the eye.

Figure 2F:
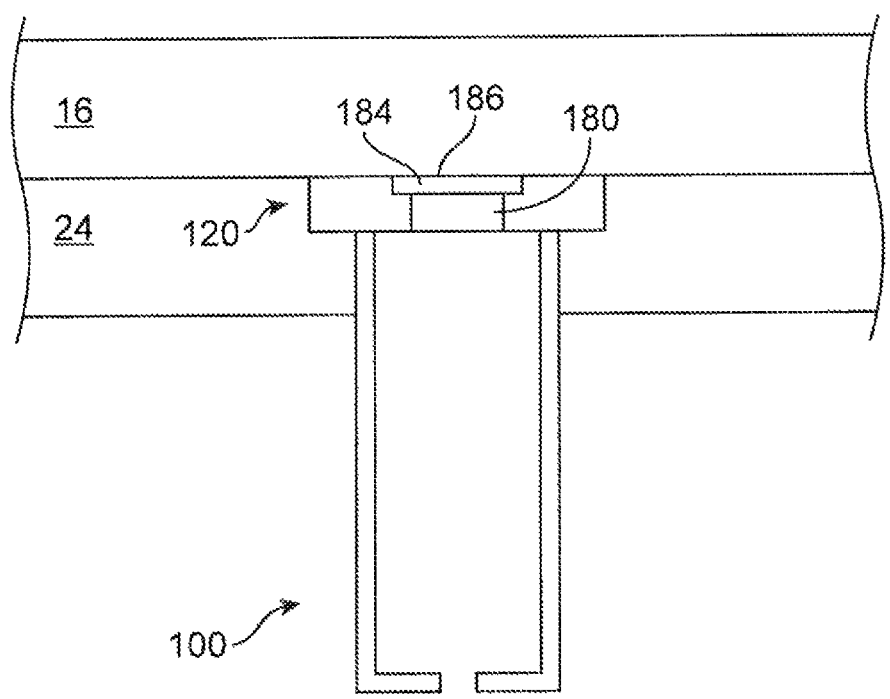
FIG. 2F shows an access port 180 suitable for incorporation with the therapeutic device 100.
Figure 3:
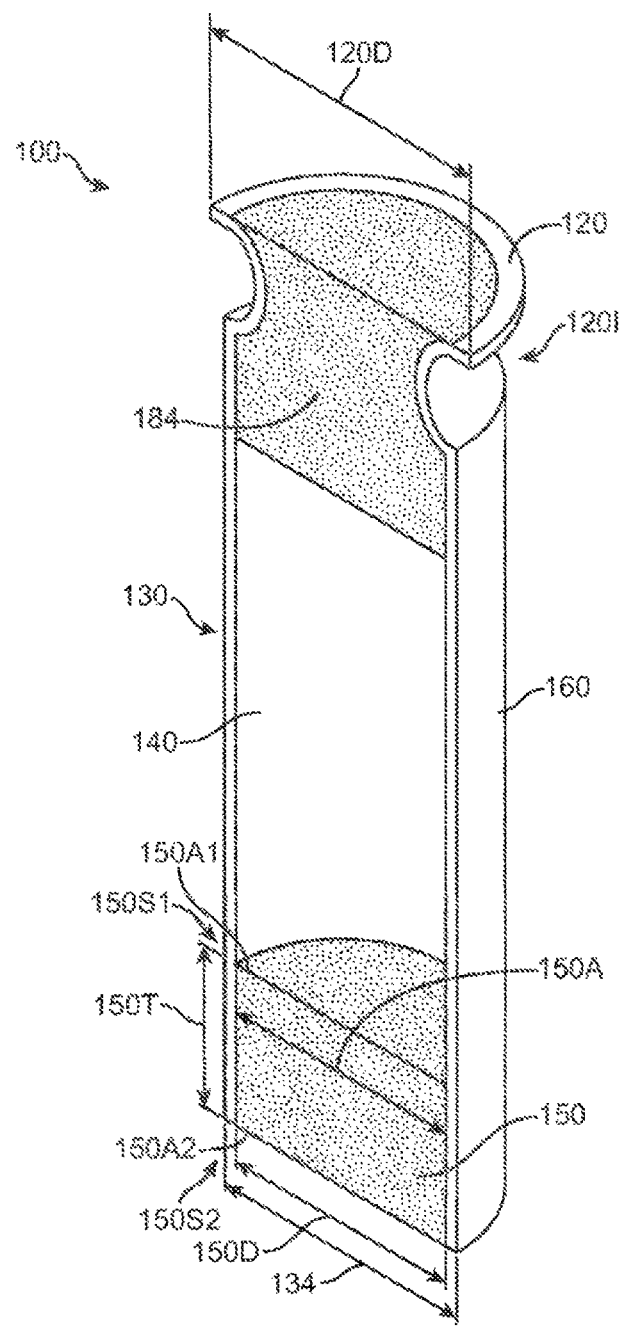
FIG. 3 shows a therapeutic device comprising a reservoir having a penetrable barrier disposed on a first end, a porous structure disposed on a second end to release therapeutic agent for an extended period, and a retention structure comprising an extension protruding outward from the container to couple to the sclera and the conjunctiva.

FIG. 2F shows an access port 180 suitable for incorporation with the therapeutic device 100. The access port 180 is combined with the therapeutic devices described herein. The access port is disposed on a proximal end of the device. The access port 180 comprises an opening formed in the retention structure 120 with a penetrable barrier 184 comprising a septum 186 disposed thereon. The penetrable barrier receives the needle 189 sized to pass the formulation 190 as described herein. The access port 180 is configured for placement under the conjunctiva 16 of the patient and above the sclera 24.

Delivery of Therapeutic Agent from Device

The drug delivery formulations of the present disclosure is contained in a reservoir chamber coupled to a porous structure in a therapeutic agent delivery system for controlled release of the therapeutic agent in the vitreous of the eye; and wherein the controlled release of the formulation from the porous structure produces a concentration of the therapeutic agent in the vitreous that is lower than the concentration of the therapeutic agent in the reservoir chamber by at least two orders of magnitude. The reservoir chamber is re-Tillable and is re-filled with the formulation after the device is inserted into the eye.

The reservoir chamber is re-filled with the formulation after the device has been in the eye for between 30-90 days, or up to 6 months. The delivery device for use in delivering any one of the formulations of the present disclosure is disclosed in WO 2010/088548, and the disclosure in the '548 publication relating only to the delivery device is incorporated by reference herein.

Design of the therapeutic agent delivery formulations for the sustained release from the PDS implant of the current embodiments is based on several considerations. For example, therapeutic agent elution from the PDS is based on molecular diffusion through the Release Control Element (RCE), which consists of irregular shaped channels. The irregular shaped channels were described in WO 2012/065006, contents of which relating to the RCE are incorporated herein in their entireties.

Moreover, diffusion takes place both ways, i.e., from the therapeutic agent diffusing out from the filled PDS into the vitreous and from the vitreous into the PDS. This reversible diffusion allows formulation contents to equilibrate with the vitreous over time. Due to diffusion to and from the PDS and vitreous, the designed formulations have to be compatible with the vitreous components and vitreous pH. The formulations also have to be compatible with the high dilution into the vitreous upon release from the PDS reservoir.

The formulations of the current disclosure are compatible with the vitreous components and vitreous pH. The formulations described in the current embodiments are compatible with the high dilution into the vitreous upon release from the PDS reservoir.

The current disclosure provides tuning of the rate of therapeutic agent delivery from the PDS implant reservoir to achieve the desired sustained release profile and desired tissue levels. According to the current disclosure, the tuning is achieved by the design of the PDS implant, which includes a porous structure for controlling therapeutic agent release. The porous structure has porosity and tortuosity, further having geometrical dimensions, and is of materials such as titanium, polymeric, and/or coated and has functionality of the surface. The tuning of the rate of delivery is also achieved by varying the reservoir volume.

The tuning of the rate of therapeutic agent delivery depends on the formulation composition, formulation agents, pH, nature of the complexing agent, concentration of the complexing agent, formulation viscosity, and/or therapeutic agent concentration in the reservoir.

Formulations of the current disclosure are designed to produce robust and highly predictable therapeutic agent delivery characteristics and profiles. In some embodiments, the use of a selected complexing agent achieves very similar therapeutic agent delivery characteristics (such as half-life of therapeutic agent delivery from PDS reservoir) for a variety of compounds formulated in that selected complexing agent. The current disclosure provides that the half-lives of different therapeutic agents are similar within a range of the complexing agent concentrations in a formulation. The therapeutic agent delivery performance and diffusion through the PDS implant for such formulations are similar to that of the non-complexed single molecular entities.

The device for delivery of the current disclosure comprises a reservoir and a porous structure. For example, the device is the one described in WO 2012/019176, contents of which relating to the reservoir are incorporated herein in their entireties. A porous structure similar to that of the current embodiment was described in WO 2012/065006, contents of which relating to the porous structure are incorporated herein in their entireties.

In some embodiments, the porous structure comprises a first side coupled to the reservoir and a second side to couple to the vitreous. The first side comprises a first area and the second side may comprise a second area.

The volume of the reservoir comprises from about 5 µL to about 50 µL of therapeutic agent, or for example from about 10 µL to about 25 µL for example, 23 µL of therapeutic agent.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. The reservoir comprises a buffer and a suspension of a therapeutic agent comprising solubility within a range from about 1 mg/mL to about 100 mg/mL, such as from about 1 mg/mL to about 40 mg/mL.

In embodiments, the concentration of the therapeutic agent in the formulation depends on increasing the solubility of the agent in water or aqueous solutions by using any one or more of: complexing agents, pH adjusting agents, solubility/stabilizing agents, amphiphilic agents, buffering agents, non-aqueous solvents, or any combinations thereof. The therapeutic agents of these embodiments are inherently sparingly soluble (parts of solvent required for 1 part of solute=30 to 100), slightly soluble (parts of solvent required for 1 part of solute=100 to 1000), very slightly soluble (parts of solvent required for 1 part of solute=1000 to 10,000), or practically insoluble or insoluble (parts of solvent required for 1 part of solute≥10,000) in water or an aqueous solution.

The release rate index comprises many values, and the release rate index with the suspension is somewhat higher than for a solution in many embodiments, for example.

The porous structure comprises a needle stop that limits penetration of the needle. The porous structure comprises a plurality of channels configured for the extended release of the therapeutic agent. The porous structure comprises a rigid sintered material having characteristics suitable for the sustained release of the material.

The reservoir and the porous structure are configured to release therapeutic amounts of the therapeutic agent in many ways. The reservoir and the porous structure is configured to release therapeutic amounts of the therapeutic agent corresponding to a concentration of at least about 0.1 µg per ml of vitreous humor or 0.1-25 µg/day for an extended period of at least about three months. The reservoir and the porous structure is configured to release therapeutic amounts of the therapeutic agent corresponding to a concentration of at least about 0.1 µg per ml of vitreous humor and no more than about 10 µg per ml of vitreous humor for an extended period of at least about three months. In some embodiments, the therapeutic agent is a small molecule therapeutic agent suitable for sustained release.

The reservoir and the porous structure are configured to release therapeutic amounts of the therapeutic agent corresponding to a concentration of at least about 0.1 µg per ml of vitreous humor and no more than about 10 µg per ml of vitreous humor for an extended period of at least about 3 months or at least about 6 months. For example, the reservoir and the porous structure are configured to release therapeutic amounts of the therapeutic agent corresponding to a concentration of at least about 0.1 µg per ml of vitreous humor and no more than about 10 µg per ml of vitreous humor for an extended period of at least about twelve months or at least about two years or at least about three years. For example, the reservoir and the porous structure is configured to release therapeutic amounts of the therapeutic agent corresponding to a concentration of at least about 0.01 µg per ml of vitreous humor and no more than about 300 µg per ml of vitreous humor for an extended period of at least about 3 months or 6 months or 12 months or 24 months.

Formulation components added to increase the solubility of the therapeutic agents bind the therapeutic agent so strongly that efficacy at the target tissue is less than ideal in at least some instances. For example, complexing agents, such as cyclodextrin, enable formulations containing high concentrations of low water solubility therapeutic agents. However, high amounts of dilution are required in order to release the therapeutic agent, as discussed, e.g., in Stella et al., *Advanced Drug Delivery Reviews*, 36: 3-16 (1999); and Brewster and Loftsson, *Advanced Drug Delivery Reviews*, 59: 645-666 (2007). Dilutions by a factor of at least 10, often factors of at least 100 or 1000 or even 10,000 are commonly needed to release large fractions of therapeutic agent from complexes with cyclodextrin.

The therapeutic agent delivery device (PDS) combined with a formulation containing a complexing agent such as cyclodextrin offers a unique advantage over all previous applications of cyclodextrin. The reservoir and porous structure of the PDS are configured to achieve the dilutions required to release therapeutic agent from cyclodextrin complexes for extended periods of time. For example, a PDS with 23 µL volume and RRI=0.007 mm implanted into a human eye achieves dilution factors in excess of 10,000 for prolonged periods of time, for example, several months. The sustained high dilution is very different than the minimal dilution that occurs when cyclodextrin formulations are applied as topical drops to the eye. Furthermore, sustained delivery with high dilution for periods of months from the PDS is unique from the short durations (e.g., hours) corresponding to intravenous injections of cyclodextrin formulations.

In embodiments, the porous structure comprises porosity, a thickness, a channel parameter and a surface area configured to release therapeutic amounts for the extended period. For example, the porous material comprises a porosity corresponding to the fraction of void space of the channels extending within the material. For example, the porosity comprises a value within a range from about 3% to about 70%. In other embodiments, the porosity comprises a value with a range from about 5% to about 10% or from about 10% to about 25%, or for example from about 15% to about 20%. Porosity is determined from the weight and macroscopic volume or is measured via nitrogen gas adsorption.

The porous structure comprises a plurality of porous structures, and the area used in the equation for calculation comprises the combined area of the plurality of porous structures.

Indications and Methods of Treatment

Disclosed are methods for the treatment and/or amelioration of diseases or conditions of the eye, especially retinopathies and ocular neovascularization. Non-limiting examples of these diseases or conditions include diabetic macular edema, AMD, CNV, NV, DR, ocular ischemia, retinal vein occlusion (central or branch), ocular trauma, surgery induced edema, surgery induced neovascularization, cystoidmacular edema, uveitis, and the like. These diseases or conditions are characterized by changes in the ocular vasculature whether progressive or non-progressive, whether a result of an acute disease or condition, or a chronic disease or condition.

The current disclosure provides use of formulations described herein in the treatment and/or amelioration of atrophic AMD. The formulations are used in the treatment of neovascular (exudative or wet) AMD. The formulation of the current disclosure treats, prevents progression of, or ameliorates a symptom of vascular leakage and/or neovascularization in the retina.

The disclosed methods relate to preventing progression of or controlling pathologic neovascularization (NV), or treating a disease or condition that is related to the onset of NV by administering to a subject one or more of the disclosed therapeutic agents, and formulations thereof. The disclosed method relates to treating or preventing progression of NV by administering to a subject an effective amount of pharmaceutically acceptable salts of pazopanib in formulations with one or more formulation agents including: complexing agents, solubilizing/stabilizing agents, pH adjusting agents, buffering agents, amphiphilic agents, non-aqueous solvents, tonicity agents, or combinations thereof. The complexing agent for use in the formulation for treating or preventing NV is cyclodextrin, for example, CAPTISOL®.

The disclosed methods relate to preventing or controlling ocular neovascularization or treating a disease or condition that is related to the onset of ocular neovascularization by intravitreal delivery of a formulation of the current disclosure.

Another disclosed method relates to preventing or controlling retinal edema or retinal neovascularization or treating a disease or condition that is related to the onset of retinal edema or retinal neovascularization by intravitreal delivery of a formulation comprising a tyrosine kinase inhibitor and a complexing agent, for example, cyclodextrin.

The present disclosure relates to a method for delaying or preventing progression of non-proliferative retinopathy to proliferative retinopathy by intravitreal delivery of a formulation comprising a tyrosine kinase inhibitor and a complexing agent, for example, cyclodextrin.

A further disclosed method relates to treating, preventing progression of and/or controlling diabetic retinopathy, or treating a disease or condition that is associated with or caused by the onset of diabetic retinopathy, by intravitreal delivery of a formulation comprising a tyrosine kinase inhibitor, pazopanib 1 HCl or pazopanib 2 HCl, and a complexing agent, for example, cyclodextrin.

Diabetic proliferative retinopathy is characterized by neovascularization. The new blood vessels are fragile and are susceptible to bleeding. The result is scaring of the retina, as well as occlusion or total blockage of the light pathway through the eye due to the over formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Yet a further disclosed method relates to preventing or controlling diabetic macular edema or treating a disease or condition that is related to the onset of diabetic macular edema by intravitreal delivery of a formulation comprising a tyrosine kinase inhibitor and a complexing agent, for example, cyclodextrin.

General Definitions

In this specification and in the claims that follow, reference is made to a number of terms, which shall be defined to have the following meanings: All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Agent" is used herein to include any other compound that may be contained in or combined with one or more of the disclosed inhibitors that is not a therapeutically or biologically active compound. As such, an agent should be pharmaceutically or biologically acceptable or relevant (for example, an agent should generally be non-toxic to the subject). "Agent" includes a single such compound and is also intended to include a plurality of agents. For the purposes of the present disclosure the term "agent" and "carrier" are used interchangeably throughout the description of the present disclosure and said terms are defined herein as, "ingredients which are used in the practice of formulating a safe and effective pharmaceutical composition."

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the surface of the eye. Each carrier must be "acceptable" in the sense of being compatible with the other ingredients of the composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, hydroxypropylmethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) gums such as HP-guar; (22) polymers; and (23) other non-toxic compatible substances employed in pharmaceutical formulations.

The term "pharmaceutically acceptable" refers to the fact that the carrier, diluent or agent must be compatible with the other ingredients of the formulation and not deleterious to the recipient thereof.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a therapeutic agent of the present invention mitigates a disease or a disorder in a host and/or reduces, inhibits, or eliminates a particular characteristic or event associated with a disorder (e.g., vascular leakage).

Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

The term "ameliorating a symptom" or other forms of the word such as "ameliorate a symptom" is used herein to mean that administration of a therapeutic agent of the present invention mitigates one or more symptoms of a disease or a disorder in a host and/or reduces, inhibits, or eliminates a particular symptom associated with the disease or disorder prior to and/or post administration of the therapeutic agent.

The disclosed compounds affect vascular leakage by inhibiting a receptor tyrosine kinase.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if a range of 10 and 15 is disclosed, then 11, 12, 13, and 14 are also disclosed.

The phrase "pharmaceutically acceptable salt(s)," as used herein, unless otherwise indicated, includes salts of acidic or basic groups.

The term "kinase" refers to any enzyme that catalyzes the addition of phosphate groups to a protein residue; for example, serine and threonine kinases catalyze the addition of phosphate groups to serine and threonine residues.

The terms "VEGFR kinase," "VEGFR," refer to any of the vascular endothelial growth factor receptors.

The terms "VEGF signaling," and "VEGF cascade" refer to both the upstream and downstream components of the VEGF signaling cascade.

The terms "administration of a compound" or "administering a compound" refer to the act of providing a compound of the invention or pharmaceutical composition to the subject in need of treatment.

In the current disclosure "composition" and "formulation" are used interchangeably and refer to the conventional understanding, as known in the art, of a composition or formulation. "Formulation" as disclosed herein may comprise a solution, suspension, semi-solid, or semi-liquid mixtures of therapeutic agents and/or formulation excipients or formulation agents.

"Solution" according to the current disclosure is a clear, homogeneous liquid form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" according to the current disclosure is a liquid form that contains solid particles dispersed in a liquid vehicle. "Suspension" as disclosed herein contemplates any variations based on the current state of the art or variations achieved by one skilled in the art.

"Therapeutic agent delivery device" and "Port Delivery System" ("PDS") are used interchangeably in this specification. As disclosed herein, the "Therapeutic agent delivery device" or "Port Delivery System" ("PDS") contemplates any variation of the disclosed device designed to achieve similar objective of target specific delivering a therapeutic agent into a subject. For example, "Therapeutic agent delivery device" or "Port Delivery System" ("PDS") may have a design to include a membrane, an opening, a diffusion barrier, a diffusion mechanism so as to release therapeutic amounts of therapeutic agent for extended periods of time, e.g., 30 days, 60 days, 90 days, 120 days or more. Several variations of the device have been disclosed in WO 2012/065006, WO2012/019047, WO2013/003620, WO 2012/019136, WO 2012/019176, and U.S. Pat. No. 8,277,830, each of which is incorporated by reference herein in its entirety.

The term "acute" as used herein denotes a condition having a rapid onset, and symptoms that are severe but short in duration.

The term "analgesic" as used herein denotes a compound/formulation for the management of intermittent and/or chronic physical discomfort, suitable for long term use.

The term "anesthetic" or "anesthesia" as used herein denotes a compound/formulation for the management of acute physical pain, suitable for short term, temporary use, which has an effect that produces numbing or decreased sensitivity in the body part/organ to which the compound/formulation is administered (e.g., decreased corneal sensitivity of the eye).

The term "aqueous" typically denotes an aqueous composition wherein the carrier is to an extent of >50%, more preferably >75% and in particular 90% by weight water.

The term "chronic" as defined herein is meant a persistent, lasting condition, or one marked by frequent recurrence, preferably a condition that persists/recurs for greater than 3 months, more preferably greater than 6 months, more preferably greater than 12 months, and even more preferably greater than 24 months.

The term "comfortable" as used herein refers to a sensation of physical well-being or relief, in contrast to the physical sensation of pain, burning, stinging, itching, irritation, or other symptoms associated with physical discomfort.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

The term "more" as used in the present disclosure does not include infinite number of possibilities. The term "more" as used in the present disclosure is used as a skilled person in the art would understand in the context in which it is used.

As used in the present disclosure, whether in a transitional phrase or in the body of a claim, the terms "comprise(s)" and "comprising" are to be interpreted as having an open-ended meaning. That is, the terms are to be interpreted synonymously with the phrases "having at least" or "including at least." When used in the context of a process the term "comprising" means that the process includes at least the recited steps, but may include additional steps. When used in the context of a molecule, compound, or composition, the term "comprising" means that the compound or composition includes at least the recited features or components, but may also include additional features or components.

For the purposes of promoting an understanding of the embodiments described herein, reference made to preferred embodiments and specific language are used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

The following examples are illustrative, but not limiting, of the methods and compositions of the present invention. Other suitable modifications and adaptations of the variety of conditions and parameters normally encountered in synthesis and use of the compounds of the present disclosure and that are obvious to those skilled in the art are within the spirit and scope of the present disclosure.

EXAMPLES

The following examples provide methods of preparing formulations of the current disclosure and evaluating their characteristics at the vitreous upon intravitreal delivery.

Example 1: Method of Preparation Pazopanib 2 HCl Formulation

The API (from Hwasun Biotechnology Corp.; Distributed by Manus-Aktteva) that contained 2 HCl per each pazopanib molecule was formulated up to 60 mg/ml drug concentrations. Pazopanib dissolved in CAPTISOL® solution and after adding all required excipients the pH was adjusted to the desired values.

Formulations were prepared by dissolving the required amount of CAPTISOL®, acid, and agents in water. Pazopanib 2 HCl was added and mixed until dissolution. Then sodium hydroxide was added to reach the final pH. Formulation was filtered and then injected into PDS implants to perform therapeutic agent release testing.

Example 2: Method of Preparation Pazopanib 1 HCl Formulation—No Lyophilization

Approximately half of the required CAPTISOL® in a vial was weighed and dissolved in the appropriate amount of water. PVP-10k (polyvinyl pyrrolidone, MW=10 kDa) and Histidine HCl were added and dissolved by mixing the solution (vortex, sonication, shaking). Pazopanib API (from Hetero Labs Limited) was weighed and then added to the CAPTISOL® solution. If needed, small amount of hydrochloric acid (HCl) was added to adjust and maintain the pH of the solution at equal to or lower than pH=2. Additives such as triacetin or glycerol were added. The formulation was stirred and shaken at 37° C. or at room temperature until pazopanib was completely dissolved. The dissolution of pazopanib can take several hours. Next, the pH of the pazopanib-CAPTISOL® solution was adjusted to pH 6-7 by adding NaOH or Meglumine. Remaining CAPTISOL® was then added and dissolved completely by shaking/vortex the formulation at 37° C. or at room temperature. The pH was checked and, if needed, adjusted, before filtering the formulation using a 0.2 μm filter. The formulation was stored at room temperature and protected from light. Content and purity of the formulation was tested by HPLC and UV.

Example 3

A high concentration formulation of a therapeutic agent, e.g., pazopanib 1 HCl was prepared by stirring and/or shaking the active pharmaceutical ingredient in a dispersion with a base, e.g. NaOH, at room temperature, for about 30 minutes. The composition of the dispersion was, e.g., about 275 mg/mL in 1N NaOH.

In this method, formulations were prepared by dissolving the required amount of cyclodextrin, acid, and agents in water. The NaOH treated pazopanib 1 HCl was added and mixed until dissolution. Then sodium hydroxide was added to reach pH 6-7. Formulation was filtered and then injected into PDS implants to perform therapeutic agent release testing.

While comparable high drug concentrations were achieved with both the 2 HCl and 1 HCl Pazopanib forms, the 1 HCl Pazopanib formulations were very unstable. The 1 HCl pazopanib readily crystallized out both from the formulation on shelf (i.e., during storage) and upon dilution of the formulation (i.e., during drug release).

The stability of the 1 HCl Pazopanib formulations was improved by lowering the drug concentration to below 40 mg/mL. See Table 5.

Example 4

For stability improvement, as well as for easier formulation process, lyophilization of the pazopanib 1 HCl was performed before solubilization in one or more formulation agents. Lyophilization was performed from trifluoro ethanol (TFE), trifluoro ethanol-water (90-10) mixture or from dimethyl sulfoxide (DMSO). Lyophilization is believed to transfer the highly crystalline drug to mostly amorphous solid, which has more favorable solubility properties. XRPD analysis was performed to compare the crystalline structure of the 2 HCl, 1 HCl and the 1 HCl lyophilized drug products; the result is shown in Table 3. The lyophilization method is summarized in Table 4.

Method of Preparation pazopanib 1 HCl Formulation—DMSO Lyophilization

Lyophilization from DMSO: About 20-60 mg/mL of a pazopanib 1 HCl solution in DMSO (dimethyl sulfoxide) was prepared. The solution was then freeze-dried under conditions well known in the art. The solution was dried under 35° C.-50° C. (e.g., at about 40° C.) for about 12 hours to about 24 hours, and about 50° C.-65° C. (e.g., at about 60° C.) for about 24 hours to about 40 hours, and at about 90° C.-110° C. (e.g., at about 100° C.) for about 0.5 hours to about 2 hours.

Method of Preparation Pazopanib 1 HCl Formulation—TFE Lyophilization

The crystalline form of about 60 mg/mL pazopanib 1 HCl in trifluoro ethanol was prepared. About 1% to about 30% water (e.g., about 20%) water was also added to the solution of the therapeutic agent solution in trifluoro ethanol. The solution was then freeze dried (with or without the added water) under standard condition in the art. The solution was dried under 35° C.-50° C. (e.g., about 40° C.) for about 12 hours to about 24 hours or at about and 50° C.-65° C. (e.g., at about 60° C.) for about 4 hours to about 8 hours.

For both the DMSO and TFE lyophilized pazopanib 1 HCl a one-step or a two-step formulation method was used to prepare the formulations.

One-Step: When native pH was used, i.e., no pH adjustment of viscous solution was necessary, the solubilization of the pharmaceutical ingredient were performed in one step. PVP-10k (polyvinyl pyrrolidone, MW=10 kDa) and Histidine HCl were weighed and dissolved in the appropriate amount of water by mixing the solution (vortex, shaking). CAPTISOL® was weighed, added and dissolved in the solution with shaking, vortexing the solution. Lyophilized pazopanib was weighed and then added to the CAPTISOL® solution and dissolved completely by vortex, sonication, shaking at ambient or at elevated (e.g., about 37° C.-50° C.) temperatures. The formulation was filtered using a 0.2 um filter and stored at room temperature and protected from light.

In another method all solid excipients (CAPTISOL®, PVP and Histidine-HCl) and the therapeutic agent (pazopanib 1 HCl) were measured and mixed together first in a vial. Using continuous mixing, gradual addition of the required water is performed. The solubilization of the formed dispersion can be done at ambient or elevated temperatures (e.g., about 37° C.-50° C.); using elevated temperatures can reduce the time needed to achieve homogeneous solutions (e.g., about 24 hours-4 hours). The formulation can be used as is (native pH 3-4) or after pH adjustment with NaOH solution (pH 6-7).

Two-Step formulation process using the lyophilized therapeutic agent: Approximately half of the required CAPTISOL® in a vial was weighed and dissolved in the appropriate amount of water. PVP-10k (polyvinyl pyrrolidone, MW=10 kDa) and Histidine HCl were added and dissolved by mixing the solution (vortex, sonication, shaking). Lyophilized pazopanib 1 HCl (lyophilized from TFE or DMSO) was weighed and then added to the CAPTISOL® solution. If needed, small amount of hydrochloric acid (HCl) was added to adjust and maintain the pH of the solution at equal to or lower than pH=2. Additives such as triacetin or glycerol were added. The formulation was stirred and shaken at 37° C. or at room temperature until pazopanib was completely dissolved. The dissolution of pazopanib can take several hours. Next, the pH of the pazopanib-CAPTISOL® solution was adjusted to pH 6-7 by adding NaOH. Remaining CAPTISOL® was then added and dissolved completely by shaking/vortex the formulation at 37° C. or at room temperature. The pH was checked and, if needed, adjusted, before filtering the formulation using a 0.2 µm filter. The formulation was stored at room temperature and protected from light. Content and purity of the formulation was tested by HPLC and UV.

Example 5

Therapeutic agent release testing was performed by measuring the amount of therapeutic agent released by the PDS into a fluid representative of vitreous, maintained at 37° C. in an incubator. The PDS was suspended in a container containing phosphate buffered saline. Periodically, the PDS was transferred into a new container and the concentration of therapeutic agent was measured in the fluid of the previous container. Rates were calculated from the amount of therapeutic agent released divided by the sample collection duration. The percent cumulative release was calculated from the cumulative amount of therapeutic agent divided by the amount of therapeutic agent initially filled into the therapeutic device (PDS). The half-life was calculated from the percent cumulative release at 4 weeks.

Therapeutic agent release was performed on pazopanib 1 HCl or 2 HCl formulated with CAPTISOL®. The formulations were filled into therapeutic devices (PDS) having reservoir volume of 23 µL. Chloride content comparison of the pazopanib samples are shown in Table 2. XRD results are shown in Table 3.

Drug release comparison: Therapeutic agent release rate was tested by measuring the amount of therapeutic agent released by the PDS into receiver fluid (PBS buffer) at 37° C. Therapeutic agent release testing was performed by measuring the amount of therapeutic agent released by the PDS into a fluid representative of vitreous, maintained at 37° C. in an incubator. The PDS was suspended in a container containing phosphate buffered saline. Periodically, the PDS was transferred into a new container and the concentration of therapeutic agent was measured in the fluid of the previous container. Rates were calculated from the amount of therapeutic agent released divided by the sample collection duration. The percent cumulative release was calculated from the cumulative amount of therapeutic agent divided by the amount of therapeutic agent initially filled into the therapeutic device (PDS). The half-life was calculated from the percent cumulative release at 4 weeks. Results are shown in FIG. 1 and summarized below:

Example 6

Precipitation test—comparative results: This test was performed with the aim to model the conditions upon drug release, i.e., when a small amount of formulation is released into a large amount of buffer solution. In the model, if the drug precipitated out upon dilution (release) that can cause clogging of the device and/or loss of drug because the solid drug would not be measurable in the receiver fluid (also it possibly would not be accessible when released under in vivo conditions). To perform the test, the formulation was diluted 330 fold with phosphate buffered saline solution (with about 0.1% sodium azide), e.g., 3 µL of formulation is added to 1 mL PBS buffer. The solution was kept in a 37° C. thermostat and periodically checked for appearance of crystal growth/precipitation. The formulations prepared from different drug sources exhibited different stability against precipitation upon dilution, as summarized in Table 5.

INCORPORATION BY REFERENCE

The entire disclosure of each of the patent documents and scientific articles referred to herein is incorporated by reference for all purposes. In the present disclosure the host document is identified with sufficient particularity and materials that are relevant to the disclosure is construed based on the context of the reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and the foregoing description and examples are for purposes of illustration and not limitation of the claims that follow.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A pharmaceutical solution comprising:
(i) β-cyclodextrin sulfobutyl ether, hydroxypropyl β-cyclodextrin, or a combination thereof;
(ii) about 0.2% to about 1.0% of polyvinylpyrrolidone; and

| Pazopanib - 2HCl Sample 1 in CAPTISOL ®(PA-96) | Pazopanib - 1HCl Sample 2 in CAPTISOL ®(PA-110) | Pozopanib - 1HCl Lyophilized From TFE (PAL-18) | Pozopanib - 1HCl Lyophilized from DMSO (PAD-5) |
|---|---|---|---|
| 60.0 mg/mL Pazopanib, 2.2:1 CAPTISOL ® 1% PVP 6 mg/ml Histidine HCl pH 6 | 60.0 mg/mL Pazopanib, 2.2:1 CAPTISOL ® 1% PVP 6 mg/ml Histidine HCl, pH 6.5 | 36 mg/mL Pazopanib, 4:1 CAPTISOL ® 1% PVP 25 mg/ml Histidine HCl, pH 6.5 | 50 mg/mL Pazopanib 3:1 CAPTISOL ® 1% PVP 6 mg/ml Histidine HCl, pH 3.4 |
| Half-Life = 53 days | Half-Life = 99 days; visible drug precipitation during release | Half-Life = 45 days | Half-life = 45 days |

(iii) about 30 mg/mL to about 60 mg/mL of an ophthalmic therapeutic agent having a solubility of less than 1 mg/mL in water;
wherein the weight ratio of (i) to (iii) is from about 2:1 to about 8:1.

2. The pharmaceutical solution of claim 1, comprising from about 30 mg/mL to about 40 mg/mL of the ophthalmic therapeutic agent.

3. The pharmaceutical solution of claim 1, comprising from about 40 mg/mL to about 60 mg/mL of the ophthalmic therapeutic agent.

4. The pharmaceutical solution of claim 1, wherein the ophthalmic therapeutic agent has a solubility of less than 0.01 mg/mL in water.

5. The pharmaceutical solution of claim 1, wherein the ophthalmic therapeutic agent is in the form of a pharmaceutically acceptable salt.

6. A pharmaceutical solution comprising:
(i) hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or a combination of two or more thereof,
(ii) about 0.1% to about 5.0% of trehalose, methylcellulose, ethylcellulose, sodium carboxymethylcellulose, sodium hyaluronate, sodium alginate, polyethylene glycol, glycerin, propylene glycol, triacetin, N,N-dimethylacetamide, polyvinylpyrrolidone, pyrrolidone, or a combination of two or more thereof; and
(iii) about 30 mg/mL to about 70 mg/mL of an ophthalmic therapeutic agent having a solubility of less than 1 mg/mL in water.

7. The pharmaceutical solution of claim 6, comprising from about 40 mg/mL to about 60 mg/mL of the ophthalmic therapeutic agent.

8. The pharmaceutical solution of claim 6, comprising from about 30 mg/mL to about 60 mg/mL of the ophthalmic therapeutic agent.

9. The pharmaceutical solution of claim 6, wherein the ophthalmic therapeutic agent has a solubility of less than 0.01 mg/mL in water.

10. The pharmaceutical solution of claim 6, wherein the weight ratio of (i) to (iii) is from about 2:1 to about 9:1.

11. The pharmaceutical solution of claim 6, wherein the-ophthalmic therapeutic agent is in the form of a pharmaceutically acceptable salt.

12. A pharmaceutical solution comprising (i) a cyclodextrin, and (ii) about 30 mg/mL to about 90 mg/mL of an ophthalmic therapeutic agent having a solubility of less than 1 mg/mL in water.

13. The pharmaceutical solution of claim 12, comprising from about 30 mg/mL to about 70 mg/mL of the ophthalmic therapeutic agent.

14. The pharmaceutical solution of claim 12, comprising from about 30 mg/mL to about 60 mg/mL of the ophthalmic therapeutic agent.

15. The pharmaceutical solution of claim 12, wherein the weight ratio of the cyclodextrin to the ophthalmic therapeutic agent is from about 2:1 to about 9:1.

16. The pharmaceutical solution of claim 12, wherein the cyclodextrin is hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or a combination of two or more thereof.

17. The pharmaceutical solution of claim 12, wherein the cyclodextrin is β-cyclodextrin sulfobutyl ether, hydroxypropyl β-cyclodextrin, or a combination thereof.

18. The pharmaceutical solution of claim 12, further comprising trehalose, methylcellulose, ethylcellulose, sodium carboxymethylcellulose, sodium hyaluronate, sodium alginate, polyethylene glycol, glycerin, propylene glycol, triacetin, N,N-dimethylacetamide, polyvinylpyrrolidone, pyrrolidone, or a combination of two or more thereof.

19. The pharmaceutical solution of claim 12, wherein the ophthalmic therapeutic agent has a solubility of less than 0.01 mg/mL in water.

20. The pharmaceutical solution of claim 12, wherein the ophthalmic therapeutic agent is in the form of a pharmaceutically acceptable monovalent salt or divalent salt.

* * * * *